(12) United States Patent
Shaked

(10) Patent No.: US 12,016,900 B2
(45) Date of Patent: *Jun. 25, 2024

(54) METHOD OF TREATING CANCER WITH AN IMMUNE CHECKPOINT INHIBITOR IN COMBINATION WITH ANOTHER THERAPEUTIC AGENT

(71) Applicant: Rappaport Family Institute for Research in the Medical Sciences, Haifa (IL)

(72) Inventor: Yuval Shaked, Binyamina (IL)

(73) Assignee: Rappaport Family Institute for Research in the Medical Sciences, Haifa (IL)

(*) Notice: Subject to any disclaimer, the term of this patent is extended or adjusted under 35 U.S.C. 154(b) by 0 days.

This patent is subject to a terminal disclaimer.

(21) Appl. No.: 16/712,816

(22) Filed: Dec. 12, 2019

(65) Prior Publication Data

US 2020/0316173 A1 Oct. 8, 2020
US 2022/0193194 A9 Jun. 23, 2022

Related U.S. Application Data

(63) Continuation-in-part of application No. 16/219,203, filed on Dec. 13, 2018, which is a continuation-in-part of application No. PCT/IL2018/050609, filed on Jun. 4, 2018.

(60) Provisional application No. 62/594,141, filed on Dec. 4, 2017, provisional application No. 62/564,392, filed on Sep. 28, 2017, provisional application No. 62/514,851, filed on Jun. 4, 2017.

(51) Int. Cl.
| | |
|---|---|
| *G16H 20/10* | (2018.01) |
| *A61K 31/38* | (2006.01) |
| *A61K 38/17* | (2006.01) |
| *A61P 35/00* | (2006.01) |
| *C07K 16/22* | (2006.01) |
| *C07K 16/28* | (2006.01) |
| *G16B 15/20* | (2019.01) |
| *A61K 45/06* | (2006.01) |

(52) U.S. Cl.
CPC .......... *A61K 38/1774* (2013.01); *A61K 31/38* (2013.01); *A61P 35/00* (2018.01); *C07K 16/22* (2013.01); *C07K 16/2818* (2013.01); *C07K 16/2827* (2013.01); *G16B 15/20* (2019.02); *G16H 20/10* (2018.01); *A61K 45/06* (2013.01)

(58) Field of Classification Search
CPC .................................................. A61K 38/1774
USPC ..................................................... 435/7.23
See application file for complete search history.

(56) References Cited

U.S. PATENT DOCUMENTS

| | | | |
|---|---|---|---|
| 5,595,756 A | 1/1997 | Bally et al. | |
| 11,155,614 B2 | 10/2021 | Shaked et al. | |
| 2016/0024585 A1 | 1/2016 | Nixon et al. | |
| 2017/0114125 A1 | 4/2017 | Sabbadini et al. | |

FOREIGN PATENT DOCUMENTS

| | | |
|---|---|---|
| AU | 2016250478 A1 | 11/2016 |
| JP | 2008502326 A | 1/2008 |
| JP | 2011526674 A | 10/2011 |
| JP | 2015512612 A | 4/2015 |
| JP | 2015516806 A | 6/2015 |
| JP | 2016-520800 B2 | 7/2016 |
| JP | 2016535275 A | 11/2016 |
| JP | 2019503386 A | 2/2019 |
| WO | 2005119260 A2 | 12/2005 |
| WO | 2009032084 A1 | 3/2009 |
| WO | 2012151574 A1 | 11/2012 |
| WO | 2013106765 A1 | 7/2013 |
| WO | 2013148288 A1 | 10/2013 |
| WO | 2016156501 A1 | 10/2016 |
| WO | 2017011907 A1 | 1/2017 |
| WO | 2017024207 A1 | 2/2017 |
| WO | 2017040960 A1 | 3/2017 |
| WO | 2017091072 A1 | 6/2017 |
| WO | 2017132536 A1 | 8/2017 |
| WO | 2017140826 A1 | 8/2017 |
| WO | 2018071824 A1 | 4/2018 |
| WO | 2018104483 A1 | 6/2018 |
| WO | 2018222711 A2 | 12/2018 |
| WO | 2018225062 A1 | 12/2018 |
| WO | 2018225063 A1 | 12/2018 |

OTHER PUBLICATIONS

Rotz et al (Pediatr Blood Cancer, 2017, 64: e26642, 5 pages).*
Lee et al (Blood, 2014, 124(2): 188-195).*
Merhil et al (Frontiers in Immunology, 2018, 9, Article 1769, 1-10).*
Choudhardy et al (World Journal of Otorhinolaryngology—Head and Neck Surgery, 2016, 2: 90-97).*
Krishnamurthy et al (Stem Cells, 2014, 32(11): 2845-2857).*
Yamazaki et al (Cancer Sci, 2017, 108(5): 1022-1031).*
Ragnhammar et al (Medical Oncology, 1996, 13: 161-166).*
Lavi et al (Journal of Controlled Release, 2007, 123: 123-130).*
Peng et al (Cancer Research, 2012, 72(20): 5209-5218).*
McMichael et al (Clin Canc Res, 2017, 23(2): 489-502).*
Beyar-Katz et al., Bortezomib-induced pro-inflammatory macrophages as a potential factor limiting anti-tumour efficacy. The Journal of Pathology, 239(3), 262-273, 2016.

(Continued)

*Primary Examiner* — Sean E Aeder
(74) *Attorney, Agent, or Firm* — The Roy Gross Law Firm, LLC; Roy Gross

(57) ABSTRACT

A method is provided for treating a cancer patient non-responsive to treatment with a immune checkpoint inhibitor (ICI) by treating the patient with said ICI in combination with an agent that blocks the activity of a dominant factor selected among the plurality of host-driven resistance factors generated in response to treatment of the cancer patient with the ICI, these factors having a fold-change predictive of a non-favorable response of the cancer patient to the treatment with the ICI.

18 Claims, 7 Drawing Sheets

(56) References Cited

OTHER PUBLICATIONS

Chen et al., Analysis of Immune Signatures in Longitudinal Tumor Samples Yields Insight into Biomarkers of Response and Mechanisms of Resistance to Immune Checkpoint Blockade. Cancer Discovery, 6(8), 827-837, 2016.
De Henau et al., Overcoming resistance to checkpoint blockade therapy by targeting PI3Kγ in myeloid cells. Nature, 539(7629), 443-447, 2016.
De Palma et al., Macrophage Regulation of Tumor Responses to Anticancer Therapies. Cancer Cell, 23(3), 277-286, 2013.
Duraiswamy et al., Dual Blockade of PD-1 and CTLA-4 Combined with Tumor Vaccine Effectively Restores T-Cell Rejection Function in Tumors. Cancer Research, 73(12), 3591-3603, 2013.
Gajewski et al., Innate and adaptive immune cells in the tumor microenvironment. Nature Immunology, 14(10), 1014-1022, 2013.
Katz et al., "Host effects contributing to cancer therapy resistance" Drug Resist Updat. 19:pp. 33-42. (2015).
Kim et al., Assaying Cell Cycle Status Using Flow Cytometry. Current Protocols in Molecular Biology, 111: 28 6 pp. 1-11. (2015).
Kim et al., "Macrophages and mesenchymal stromal cells support survival and proliferation of multiple myeloma cells", British Journal of Haematology; 158(3): pp. 336-346. (2012).
Kodumudi et al., "Immune Checkpoint Blockade to Improve Tumor Infiltrating Lymphocytes for Adoptive Cell Therapy" PloS one 11(4):e0153053. (2016).
Ma et al., "Anticancer Chemotherapy-Induced Intratumoral Recruitment and Differentiation of Antigen-Presenting Cells", Immunity. 38(4): pp. 729-741 (2013).
Makkouk et al., "Cancer Immunotherapy and Breaking Immune Tolerance—New Approaches to an Old Challenge", Cancer Res. 75(1): pp. 5-10 (2015).
Ostrand-Rosenberg et al., "Myeloid-Derived Suppressor Cells: Linking Inflammation and Cancer", J. Immunol. 182(8): 4499-4506, 2009.
Pardoll, "The blockade of immune checkpoints in cancer immunotherapy", Nat Rev Cancer. 12(4): 252-264, (2012).
Postow et al., "Immune Checkpoint Blockade in Cancer Therapy", Journal of Clinical Oncology vol. 33, No. 17, pp. 974-982 (2015).
Romano et al., The therapeutic promise of disrupting the PD-1/PD-L1 immune checkpoint in cancer: unleashing the CD8 T cell mediated anti-tumor activity results in significant, unprecedented clinical efficacy in various solid tumors, Journal for Immuno Therapy of Cancer 3:15, 2015.
Sato et al., "Interleukin 10 in the tumor microenvironment: a target for anticancer immunotherapy", Immunol Res. 51:170-182, 2011.
Shaked, "Balancing efficacy of and host immune responses to cancer therapy: the yin and yang effects" Nat Rev Clin Oncol (2016).
Shaked et al., "Therapy-Induced Acute Recruitment of Circulating Endothelial Progenitor Cells to Tumors", Science. 313(5794):1 pp. 785-787. (2006).
Shaked et al., "Rapid Chemotherapy-Induced Acute Endothelial Progenitor Cell Mobilization: Implications for Antiangiogenic Drugs as Chemosensitizing Agents", Cancer Cell. 14(3): pp. 263-273 (2008).
Sharma, P., Hu-Lieskovan, S., Wargo, J. A., & Ribas, A. (2017). Primary, Adaptive, and Acquired Resistance to Cancer Immunotherapy. Cell, 168(4), 707-723, 2017.
Swart et al., "Combination Approaches with immune-Checkpoint Blockade in Cancer Therapy" Frontiers in Oncology. 6:233 (2016).
Topalian et al., "Immune checkpoint blockade: a common denominator approach to cancer therapy", Cancer Cell 27 (4): pp. 450-461, 2015.
Yamazaki et al.; "Cytokine biomarkers to predict antitumor responses to nivolumab suggested in a phase 2 study for advanced melanoma". Cancer science, 108.5: 1 pp. 022-1031.(2017).
Hamid et al., A prospective phase II trial exploring the association between tumor microenvironment biomarkers and clinical activity of ipilimumab in advanced melanoma. Journal of translational medicine, 9.1:204 (2011).
Bonfil et al., "Inhibition of human prostate cancer growth, osteolysis and angiogenesis in a bone metastasis model by a novel mechanism-based selective gelatinase inhibitor", Int. J. Cancer: 118, 2721-2726 (2006).
Fujiu et al., "A heart-brain-kidney network controls adaptation to cardiac stress through tissue macrophage activation" Nature Medicine, vol. 23, No. 5, 611-622, 2017.
Kruger et al., Antimetastatic Activity of a Novel Mechanism-Based Gelatinase Inhibitor; Cancer Res 2005; 65: (9), 3523-3526, 2005.
Munoz et al., Highly Efficacious Nontoxic Preclinical Treatment for Advanced Metastatic Breast Cancer Using Combination Oral UFTCyclophosphamide Metronomic Chemotherapy, Cancer Res 2006; 66: (7), 3386-3391, 2006.
Juric et al., "MMP-9 inhibition promotes anti-tumor immunity through disruption of biochemical and physical barriers to T-cell trafficking to tumors", PLOS One 13(11), 2018.
Tockman et al., "Considerations in Bringing a Cancer Biomarker to Clinical Application", Cancer Research, 52:2711s-2718s, 1992.
Sanmamed et al., "Serum Interleukin-8 Reflects Tumor Burden and Treatment Response across Malignancies of Multiple Tissue Origins", Clinical Cancer Research, 20(22), 5697-5707, 2014.
Dronca et al., "Bim and soluble PD-L1 (sPD-L1) as predictive biomarkers of response to anti-PD-1 therapy in patients with melanoma and lung carcinoma", Journal of Clinical Oncology, 35, No. 15, suppl, Abstract, 11534, 2017.
Sznol et al., "Survival and long-term follow-up of safety and response in patients (pts) with advanced melanoma (MEL) in a phase I trial of nivolumab" Journal of Clinical Oncology, 31, No. 18, suppl, Abstract, CRA9006/\, 2013.
Chen et al. (2012). Role of Interleukin-6 in the Radiation Response of Liver Tumors. Int J Radiation Oncol Biol Phys, vol. 84, No. 5, pp. e621-e630; DOI: 10.1016/j.ijrobp.2012.07.2360.
Sheng et al. (2015). The Relationship Between Serum Interleukin-6 and the Recurrence of Hepatitis B Virus Related Hepatocellular Carcinoma after Curative Resection, Medicine (Baltimore). Jun. 2015; 94(24): e941; DOI: 10.1097/MD.0000000000000941.
Skolnick et al. (2000). From genes to protein structure and function: novel applications of computational approaches in the genomic era. Trends Biotechnol. Jan. 2000; 18 (1):34-9; doi: 10.1016/s0167-7799(99)01398-0.
Burgess et al. (1990). Possible Dissociation of the Heparin-binding and Mitogenic Activities of Heparin-binding (Acidic Fibroblast) Growth Factor-1 from its Receptor-binding Activities by Site-Directed Mutagenesis of a Single Lysine Residue. J. Cell Biol. 111: 2129-2138. DOI: 10.1083/jcb.111.5.2129.
Miosge (2015). Comparison of predicted and actual consequences of missense mutations. Proc Natl Acad Sci U S A. 2015; 112(37): E5189-98; https://doi.org/10.1073/pnas.1511585112.
Bork (2000). Powers and pitfalls in sequence analysis: The 70% Hurdle. Genome Research, 10:398-400; DOI: 10.1101/gr.10.4.398.
Warzocha et al. (1997). Antisense Strategy: Biological Utility and Prospects in the Treatment of Hematological Malignancies. Leukemia and Lymphoma (1997) vol. 24. pp. 267-281; DOI: 10.3109/10428199709039014.
McKeague et al. (2012). Challenges and Opportunities for Small Molecule Aptamer Development. J Nucleic Acids. 2012;2012:748913, Epub Oct. 24, 2012; DOI: 10.1155/2012/748913.
Vajdos et al. (2022). Comprehensive Functional Maps of the Antigen-binding Site of an Anti-ErbB2 Antibody Obtained with Shotgun Scanning Mutagensis. J Mol Biol. Jul. 5, 2022;320(2):415-28; DOI: 10.1016/S0022-2836(02)00264-4.
Brown et al. (1996). Tolerance to Single, but Not Multiple, Amino Acid Replacements in Antibody VH, CDR2. J Immunol. May 1996; 156(9):3285-91; PMID: 8617951.
Guido et al. (2008). Virtual Screening and Its Integration with Modern Drug Design Technologies, Curr Med Chem. 2008; 15(1): 37-46; DOI: 10.2174/092986708783330683.
Clark et al. (2014). Discovery and Development of Janus Kinase (JAK) Inhibitors for Inflammatory Diseases. J. Med. Chem., 2014, 57 (12), pp. 5023-5038; https://doi.org/10.1021/jm401490p.
Waiker et al (2012). Imperfect Gold Standards for Kidney Injury Biomarker Evaluation, J Am Soc Nephrol. Jan. 2012; 23(1): 13-21; DOI: 10.1681/ASN.2010111124.

(56) References Cited

OTHER PUBLICATIONS

Brooks (2012). Translational genomics: The challenge of developing cancer biomarkers. Genome Res. 2012. 22: 183-187; doi: 10.1101/gr.124347.111.
McKean et al. (2020). Biomarkers in Precision Cancer Immunotherapy: Promise and Challenges. Am Soc Clin Oncol Educ Book. May 2020;40:e275-e291; DOI: 10.1200/EDBK_280571.
Aberuyi et al. (2019). Drug Resistance Biomarkers and Their Clinical Applications in Childhood Acute Lymphoblastic Leukemia. Front Oncol. 2019; 9: 1496; doi: 10.3389/fonc.2019.01496.
Sporn et al. (2000). Chemoprevention of Cancer, Carcinogenesis, vol. 21 (2000) 525-530; DOI: 10.1093/carcin/21.3.525.
Auerbach et al. (2000). Angiogeneis assays: Problems and Pitfalls. Cancer and Metasis Reviews, 2000, 19: 167-172; DOI: 10.1023/a:1026574416001.
Gura, T. (1997). Systems for Identifying New Drugs are Often Faulty. Science, 1997, 278(5340): 1041-1042; DOI: 10.1126/science.278.5340.1041.
HogenEsch et al. (2012). Challenges in pre-clinical testing of anti-cancer drugs in cell culture and in animal models, J Control Release. Dec. 10, 2012; 164(2): 183-186. DOI: 10.1016/j.jconrel.2012.02.031.
Efferth, Thomas, et al. (2006). Expression profiling of ATP-binding cassette transporters in childhood T-cell acute lymphoblastic leukemia, Molecular Cancer Therapeutics 2006;5(8); DOI: 10.1158/1535-7163.MCT-06-0086.
Goncalves, Kevin A., et al. (2016). Angiogenin Promotes Hematopoietic Regeneration by Dichotomously Regulating Quiescence of Stem and Progenitor Cells, Cell Press 166, 894-906; DOI: 10.1016/j.cell.2016.06.042.
Pierard, Laure et al. (2017) Involvement of Angiogenin in Sunitinib Resistance in Human Renal Cell Carcinoma, The Journal of Urology vol. 197, No. 4S, Supplement. https://doi.org/10.1016/j.juro.2017.02.3352.
Wei, Jin, et al. (2017) MUC1 induces acquired chemoresistance by upregulating ABCB1 in EGFR-dependent manner, Cell Death and Disease 8, e2980, 13 pages; https://doi.org/10.1038/cddis.2017.378.
Winter, Stuart S., (2013) ATP Binding Cassette C1 (ABCC1/MRP1)-mediated drug efflux contributes to disease progression in T-lineage acute lymphoblastic leukemia, Health (Irvine Calf) 5(5A): 41-50; DOI: 10.4236/health.2013.55A005.
Alishekevitz et al., (2016). Macrophage-Induced Lymphangiogenesis and Metastasis following Paclitaxel Chemotherapy Is Regulated by VEGFR3. Cell Reports, 17(5), 1344-1356; DOI: 10.1016/j.celrep.2016.09.083.
Chen et al. (2014). Intermittent Metronomic Drug Schedule Is Essential for Activating Antitumor Innate Immunity and Tumor Xenograft Regression. Neoplasia, 16(1), 84-W27; DOI: 10.1593/neo.131910.
Doloff et al. (2012) VEGF Receptor Inhibitors Block the Ability of Metronomically Dosed Cyclophosphamide to Activate Innate Immunity-Induced Tumor Regression. Cancer Research, 72(5), 1103-1115; DOI: 10.1158/0008-5472.CAN-11-3380.
Giesen et al. (2014). Highly multiplexed imaging of tumor tissues with subcellular resolution by mass cytometry. Nature Methods, 11(4), 417-422; https://doi.org/10.1038/nmeth.2869.
Gingis-Velitski et al. (2011). Host Response to Short-term, Single-Agent Chemotherapy Induces Matrix Metalloproteinase-9 Expression and Accelerates Metastasis in Mice. Cancer Research, 71(22), 6986-6996, 2011. DOI: 10.1158/0008-5472.CAN-11-0629.
Hughes et al. (2010). Matrigel: A complex protein mixture required for optimal growth of cell culture. Proteomics, 10(9), 1886-1890, 2010. https://doi.org/10.1002/pmic.200900758.
Kruisbeek, A. M. (1992). In Vivo Depletion of CD4- and CD8-Specific T Cells. Current Protocols in Immunology, 1(1), 4.1.1-4.1.5, 2001; https://doi.org/10.1002/0471142735.im0401s01.
Qiu et al. (2011). Extracting a Cellular Hierarchy from High-dimensional Cytometry Data with SPADE, Nat Biotechnol.; 29(10): 886-891, 2011; https://doi.org/10.1038/nbt.1991.

Rachman-Tzemah et al. (2017). Blocking Surgically Induced Lysyl Oxidase Activity Reduces the Risk of Lung Metastases, Cell Reports; 19(4): pp. 774-784. DOI: 10.1016/j.celrep.2017.04.005.
Ran et al. (2013). Double nicking by RNA-guided CRISPR Cas9 for enhanced genome editing specificity, Cell. 12; 154(6): 1380-1389; DOI: 10.1016/j.cell.2013.08.021.
Ran et al. (2013) Genome engineering using the CRISPR-Cas9 system, Nat Protoc. 8(11): 2281-2308; https://doi.org/10.1038/nprot.2013.143.
Shaked et al., Antiangiogenic Strategies on Defense: On the Possibility of Blocking Rebounds by the Tumor Vasculature after Chemotherapy, Cancer Res. 67(15): pp. 7055-7058 (2007); https://doi.org/10.1158/0008-5472.CAN-07-0905.
Sun et al. (2015). IL-10 and PD-1 cooperate to limit the activity of tumor-specific CD8 + T cells, Cancer Res. 75(8): 1635-1644. DOI: 10.1158/0008-5472.CAN-14-3016.
Timaner et al. (2016). Analysis of the Stromal Cellular Components of the Solid Tumor Microenvironment Using Flow Cytometry, Curr Protoc Cell Biol. 70:19 pp. 81-82 (2016). DOI: 10.1002/0471143030.cb1918s70.
Tian et al. (2016) A novel cancer vaccine with the ability to simultaneously produce anti-PD-1 antibody and GM-CSF in cancer cells and enhance Th1-biased antitumor immunity, Signal Transduction and Targeted Therapy (2016) 1, 16025; DOI: 10.1038/sigtrans.2016.25.
Karachaliou et al., "Interferon-gamma (INFG), an important marker of response to immune checkpoint blockade (ICB) in non-small cell lung cancer (NSCLC) and melanoma patients." Journal of Clinical Oncology, 2017, 35(15 suppl) Abstract 11504. DOI: 10.1200/JCO.2017.35.15_suppl.11504.
Kindler et al., "Biomarkers of pembrolizumab (P) activity in mesothelioma (MM): Results from a phase II trial." Oncology, 2017, 35 (15 suppl) Abstract 8557. DOI: 10.1200/JCO.2017.35.15_suppl.8557.
Bent, et al., "A senescence secretory switch mediated by PI3K/AKT/mTOR activation controls chemoprotective endothelial secretory responses" Genes & Development 30:1-11, 2016. http://www.genesdev.org/cgi/doi/10.1101/gad.284851.116.
InVivoMab anti-mouse IL-7R product sheet (cat. #BE002), downloaded from https://bioxcell.com/invivomab-anti-mouse-il-7ra-cd127 on Aug. 6, 2023). (Year:2023).
Wei et al., "Analysis of the role of the interleukins in colon cancer" Biological Research, (2020) 53:20, pp. 1-9. https://doi.org/10.1186/s40659-020-00287-2.
Gonnelli et al., "No effect of covalently linked poly(ethylene glycol) chains on protein internal dynamics" Biochimica et Biophysica Acta 1794 (2009) 569-576. DOI: 10.1016/j.bbapap.2008.12.005.
Lavi et al., "Sustained delivery of IL-1Ra from biodegradable microspheres reduces the number of murine B16 melanoma lung metastases" Journal of Controlled Release, 123, 2007; 123-130.
McMichael et al., "IL-21 Enhances Natural Killer Cell Response to Cetuximab-Coated Pancreatic Tumor Cells" Clinical Cancer Research, 2017, 23(2); 489-502. doi: 10.1158/1078-0432.CCR-16-0004. Epub Jul. 19, 2016. PMID: 27435400; PMCID: PMC5241232.
Peng et al., "PD-1 Blockade Enhances T-cell Migration to Tumors by Elevating IFN-y Inducible Chemokines" Cancer Research, 2012, 72(20); 5209-5218. doi: 10.1158/0008-5472.CAN-12-1187. Epub Aug. 20, 2012. PMID: 22915761; PMCID: PMC3476734.
Ragnhammar et al., "Neutralising antibodies to granulocyte-macrophage colony stimulating factor (GM-CSF) in carcinoma patients following GM-CSF combination therapy" 1996, 13; 161-166. doi: 10.1007/BF02990843. PMID: 9106175.
Lin et al. "The role of IL-7 in immunity and cancer", Anticancer Research Mar. 2017, 37 (3) 963-967. doi: 10.21873/anticanres.11405. PMID: 28314253.
Chen et al., "Siltuximab (CNTO 328): a promising option for human malignancies". Drug Design, Development and Therapy 2015:9 3455-3458. doi: 10.2147/DDDT.S86438. PMID: 26170629; PMCID: PMC4494175.
Wang et al. "IL-6 mediates platinum-induced enrichment of ovarian cancer stem cells". JCI Insight. Dec. 6, 2018; 3(23):e 122360, doi: 10.1172/jci.insight.122360. PMID: 30518684; PMCID: PMC6328027.

(56) References Cited

OTHER PUBLICATIONS

Turano et al. A Potential Role of IL-6/IL-6R in the Development and Management of Colon Cancer. Membranes (2021), 11, 312. doi: 10.3390/membranes11050312. PMID: 33923292; PMCID: PMC8145725.

Cohen et al. "Platinum-resistance in ovarian cancer cells is mediated by IL-6 secretion via the increased expression of its target cIAP-2". J Mol Med (Berl). Mar. 2013; 91 (3): 357-68. doi: 10.1007/s00109-012-0946-4. . Epub Sep. 28, 2012, PMID: 23052480.

Anonymous: "FAM83 Proteins Promote Tumorigenesis and Drug Resistance", Cancer Discovery, 2012, vol. 2, No. 10, 1 page. DOI: 10.1158/2159-8290.CD-RW2012-133.

Dronca et al., "Bim and soluble PD-L1 (sPD-L1) as predictive biomarkers of response to anti-PD-1 therapy in patients with melanoma and lung carcinoma" Journal of Clinical Oncology, 2017, 35 No. 15 suppl, Abstract 11534. DOI: 10.1200/JCO.2017.35.15_suppl. 11534.

Sanmamed et al., "Serum Interleukin-8 Reflects Tumor Burden and Treatment Response across Malignancies of Multiple Tissue Origins" Clinical Cancer Research, 2014, 20(22): 5697-5707. doi: 10.1158/1078-0432.CCR-13-3203. Epub Sep. 15, 2014. PMID: 25224278.

Sznol et al., "Survival and long-term follow-up of safety and response in patients (pts) with advanced melanoma (MEL) in a phase I trial of nivolumab (anti-PD-1; BMS-936558; ONO-4538)" Journal of Clinical Oncology, 2013, 31 No. 18 suppl, Abstract CRA9006^. DOI: 10.1200/jco.2013.31.18_suppl.cra9006.

Tockman et al., "Considerations in Bringing a Cancer Biomarker to Clinical Application" Cancer Research, 1992, 52:2711s-2718s. PMID: 1563002.

Lee et al. "Current concepts in the diagnosis and management of cytokine release syndrome," 2014, Blood, vol. 124, No. 2, pp. 188-195. doi: 10.1182/blood-2014-05-552729.

Rotz et al. "Severe cytokine release syndrome in a patient receiving PD-1-directed therapy" Pediatric Blood & Cancer, 2017, 64: e26642, 5 pages. DOI: 10.1002/pbc.26642.

Huang Chunlan et al., "Current Status of Treatment of Multiple Myeloma", Journal of Military Surgeon in Southwest China, vol. 13, No. 4, 704-707, Jul. 15, 2011.

Xiao-Yun Li et al., "Doxorubicin resistance induces IL6 activation in the colon cancer cell line LS180" Oncology Letters, 16: 5923-5929, 2018. doi: 10.3892/ol.2018.9360. PMID: 30344742; PMCID: PMC6176352.

Hirotake Tsukamoto et al., "Combined Blockade of IL6 and PD-1/PD-L1 Signaling Abrogates Mutual Regulation of Their Immunosuppressive Effects in the Tumor Microenvironment" American Association for Cancer Research, Cancer Res. Sep. 1, 2018;78(17):5011-5022. doi: 10.1158/0008-5472.CAN-18-0118. PMID: 29967259.

* cited by examiner

METHOD OF TREATING CANCER WITH AN IMMUNE CHECKPOINT INHIBITOR IN COMBINATION WITH ANOTHER THERAPEUTIC AGENT

CROSS-REFERENCE TO RELATED APPLICATIONS

This application claims the benefit of priority of non-provisional U.S. application Ser. No. 16/219,203, filed on Dec. 13, 2018. The disclosure of the prior application is considered part of and is incorporated by reference in its entirety in the disclosure of this application.

FIELD OF THE INVENTION

The present invention is in the field of oncology and particularly relates to a method of treatment of a cancer patient with an immune checkpoint inhibitor in combination with another therapeutic agent.

BACKGROUND

One of the major obstacles in clinical oncology is that tumors often develop resistance to therapy even when an initial tumor response to treatment is observed. Many studies have focused on the contribution of mutations and genetic aberrations in the tumor cells which promote drug resistance and can explain tumor re-growth. However, studies have demonstrated that the host, in response to cancer therapy, generates pro-tumorigenic and pro-metastatic effects which in turn contribute to tumor re-growth, and therefore negate the anti-tumor activity of the drug (for reviews see Katz and Shaked, 2015; Shaked, 2016).

Host-mediated responses to anti-cancer treatment modalities may be molecular and/or cellular responses. Upon treatment with chemotherapeutic drugs, host bone marrow derived cells (BMDCs) are mobilized from the bone marrow compartment, colonize the treated tumor and contribute to tumor angiogenesis and cancer re-growth, thereby promoting therapy resistance (Shaked et al., 2006, 2008). Cancer therapy also induces pro-tumorigenic activation of various immune cells such as macrophages and antigen presenting cells (Beyar-Katz et al., 2016; De Palma and Lewis, 2013; Kim et al. 2012; Ma et al., 2013). Overall, these aforementioned studies indicate that host-mediated molecular and cellular responses to different anti-cancer treatments involve the activation or education of immune cells as well as the secretion of various pro-tumorigenic factors. These combined effects contribute to tumor re-growth and resistance to therapy. This relatively new phenomenon has made a paradigm shift in understanding cancer progression and resistance to cancer therapy.

Recently, a new treatment modality, an immunotherapy using immune checkpoint inhibitors (ICIs), is revolutionizing cancer therapy. Such immune-modulating drugs have shown remarkable successes for the treatment of advanced malignancies (including stage IV) such as melanoma, prostate, non-small cell lung cancer, renal cell carcinoma and also some hematological malignancies (Postow et al., 2015). Although the human immune system is capable of recognizing and mounting a response to cancerous cells, this response is often circumvented by tumor-derived inhibition resulting in immune tolerance. In this regard, tumor-infiltrating lymphocytes (TILs), such as tumor antigen-specific $CD8^+$ cytotoxic T lymphocytes (CTLs) and natural killer (NK) cells, have been found to colonize the tumor microenvironment (Gajewski et al., 2013). Yet, at the tumor site, they completely lack the ability to act against tumor cells (Ostrand-Rosenberg and Sinha, 2009). This is due to direct inhibitory effects of factors secreted by cancer cells, stromal cells or other suppressive immune cells such as myeloid derived suppressor cells (MDSCs) and T regulatory cells (Tregs) (Makkouk and Weiner, 2015). For instance, IL-10 is frequently upregulated in various types of cancer, and was shown to suppress the immune system (Sato et al., 2011). Thus, identifying molecules that negatively regulate the immune system against tumor cells, will lead to the development of immunomodulatory drugs that support the activation of immune cells against tumors.

Of specific interest are immune checkpoint proteins, such as CTLA-4, PD-1 and its ligand, PD-L1. These checkpoint proteins are expressed by tumor cells or other immune cells and contribute to the exhaustion of CTLs (Postow et al., 2015; Topalian et al., 2015). Specifically, they keep immune responses in check, and inhibit T cell killing effects against tumor cells. As such, checkpoint inhibitors have been developed in order to inhibit the immune suppression effects. Currently, antibodies blocking the immune checkpoints CTLA-4 and PD-1 or its ligand PD-L1 have been developed (Pardoll, 2012). These ICIs are currently in use in the clinic for the treatment of various malignancies with some promising and remarkable successes (Romano and Romero, 2015). However, ICIs have shown therapeutic benefit only for a limited portion of cancer patients (~10-20%). For example, pooled data from clinical studies of ipilimumab, a CTLA-4 blocking antibody, revealed that the duration of clinical response is around 3 years, and can last up to 10 years. However, this dramatic therapeutic effect is only observed in a subset of patients (~20%). Thus, the majority of patients exhibit intrinsic resistance mechanisms to such therapies. Yet, the molecular aspects that define the subpopulation of patients that are responsive to ICIs are not fully clear. It has been suggested that markers such as PD-L1 expression by tumor cells, mutational burden, and lymphocytic infiltrates could predict the cancer patients that will respond to ICI immunotherapy. However, these aforementioned biomarkers do not always correlate with tumor responsiveness to ICI immunotherapy or resistance of patients to ICIs. Therefore, additional possible mechanisms are still unknown.

In the Applicant's International Patent Applications No. PCT/IL2018/050608 and No. PCT/IL2018/050609, both filed on Jun. 4, 2018 and published as WO2018/225062 and WO 2018/225063, respectively, the entire contents of which are hereby incorporated herein by reference, a method of predicting personalized response to cancer treatment with a cancer therapy was described by identification of a plurality of factors/biomarkers induced by the cancer patient into the circulation in response to said cancer therapy ("host response") and determining how a change in the levels of each of one or more of the plurality of factors as compared to a reference level, predicts a favorable or a non-favorable response of the cancer patient to the treatment with said cancer therapy.

It would be highly desirable to unveil host-mediated cellular and molecular mechanisms that contribute to tumor resistance to all modalities of cancer therapy including the promising ICI immunotherapy modality. This will permit development of strategies to block such unwanted host effects and will improve therapeutic outcome and delay resistance to cancer therapy.

SUMMARY OF THE INVENTION

The present invention is based on previous studies mentioned hereinbefore in the Background section of the application that show that a cancer patient (the "host"), in response to a cancer therapy, may generate and induce into the host circulation a set of host-driven resistance factors to cancer immunotherapy with an immune checkpoint inhibitor (hereinafter "ICI"), that may limit or counteract the effectiveness of the patient treatment with the ICI. The determination of these factors allows the prediction in a personalized form of the favorable or non-favorable response of the patient to the treatment with the ICI. These factors, herein designated interchangeably "factors" or "biomarkers", are factors, mainly cytokines, chemokines, growth factors, soluble receptors, enzymes and other molecules produced by the host cells, either at different organs or at the tumor microenvironment, in response to the cancer therapy with the ICI with which the patient is treated.

Thus, in one aspect, the present invention provides a method of treating a cancer patient with an immune checkpoint inhibitor (ICI), the method comprising the steps of:

(i) performing an assay on a blood sample selected from blood plasma, whole blood, blood serum or peripheral blood mononuclear cells obtained from the cancer patient at a time point after a session of treatment with said ICI, to determine the levels of one or more of a plurality of host-driven resistance factors that are driven by the host ("the cancer patient") in response to treatment with the ICI, said one or more of the plurality of factors promoting in a personalized form responsiveness or non-responsiveness of the cancer patient to the treatment with the ICI;

(ii) obtaining reference levels for each of the one or more of the plurality of the host-driven resistance factors of step (i) by determining the levels of each of said factors in a blood sample of the same type of the blood sample of step (i), obtained from the cancer patient at a time point before said session of treatment with the ICI;

(iii) establishing the fold change for each of the one or more of the plurality of the host-driven resistance factors of step (i) by comparing the level of each host-driven resistance factor of step (i) with the reference level of step (ii) for the same factor;

(iv) determining that the cancer patient has a favorable or a non-favorable response to the treatment with said ICI based on the fold change established in step (iii) for one or more of the plurality of host-driven resistance factors of step (i); and (iva) if the cancer patient has a non-favorable response to the treatment with said ICI based on the fold change established in step (iii) for one or more of the plurality of the host-driven resistance factors, then selecting a dominant factor among the one or more host-driven resistance factors showing a fold change indicative of said non-favorable response, and treating the patient with a therapeutically effective amount of the ICI along with a therapeutically effective amount of an agent that blocks the activity of the selected dominant host-driven resistance factor (herein "the dominant factor") or the receptor thereof; or (ivb) if the cancer patient has a favorable response to the treatment with said ICI based on the fold change established in (iii) for one or more of the plurality of host-driven resistance factors, then continuing the treatment of the cancer patient with the ICI alone.

In a certain embodiment, the invention relates to a method for treatment of a cancer patient non-responsive to treatment with an immune checkpoint inhibitor (ICI), the method comprising administering to the cancer patient a therapeutically effective amount of the ICI in combination with a therapeutically effective amount of an agent that blocks the activity of a dominant factor, or of the receptor thereof, the dominant factor being selected among the plurality of host-driven resistance factors generated in response to treatment of the cancer patient with the ICI, the plurality of host-driven resistance factors having a fold-change predictive of a non-favorable response of the cancer patient to the treatment with the ICI, wherein the fold change is established by comparing: (i) the level of each host-driven resistance factors in a blood sample selected from blood plasma, whole blood, blood serum or peripheral blood mononuclear cells, obtained from the cancer patient after a session of treatment with the ICI, with (ii) a reference level obtained for the same factor from a blood sample of the same type of (i), obtained from the cancer patient before said session of treatment with the ICI. Preferably, the blood samples of steps (i) and (ii) are both blood plasma.

In another aspect, the present invention relates to an immune checkpoint inhibitor (ICI), for use in the treatment of cancer in a patient non-responsive to said treatment, comprising administering a therapeutically effective amount of the ICI in combination with a therapeutically effective amount of an agent that blocks the activity of a dominant factor, or of the receptor thereof, the dominant factor being selected among the plurality of host-driven resistance factors generated in response to treatment of the cancer patient with the ICI, the plurality of host-driven resistance factors having a fold-change predictive of a non-favorable response of the cancer epatient to the treatment with the ICI, wherein the fold change is established by comparing: (i) the level of each host-driven resistance factor in a blood sample selected from blood plasma, whole blood, blood serum or peripheral blood mononuclear cells, obtained from the cancer patient after a session of treatment with the ICI, with (ii) a reference level obtained for the same factor from a blood sample of the same type of (i), obtained from the cancer patient before said session of treatment with the ICI. Preferably, the blood samples of steps (i) and (ii) are both blood plasma.

BRIEF DESCRIPTION OF THE FIGURES

FIG. 1A shows that mice treated with a combination of anti-PD-L1 and the MMP-2/MMP-9 inhibitor SB-3CT exhibit reduced tumor size compared to mice treated with vehicle, anti-PD-L1 or SB-3CT alone. FIG. 1B shows tumor volume at day 27, the last experimental day. FIG. 1C shows better response rate and reduced tumor size for individual mice treated with the combined therapy compared to anti-PD-L1 alone. FIG. 1D shows better survival of mice treated with the combined therapy compared to the other treatment groups.

FIGS. 2A-2B show tumor volume of mice treated with anti-PD-L1, anti-amphiregulin antibody (anti-AREG) or anti-PD-L1 and anti-AREG combined therapy. FIG. 2C is a Kaplan-Meier curve demonstrating better survival of mice treated with the combined therapy compared to the other treatment groups.

FIG. 4A shows inhibition in tumor growth in mice treated with a combination of anti-PD-L1 and anti-IL-6 compared to control mice or mice treated with either anti-PD-L1 or anti-IL-6 alone. FIG. 4B corresponds to FIG. 4A, but shows tumor growth in individual animals, and FIG. 4C shows that combined treatment with both anti-PD-L1 and anti-IL-6 also led to better survival relative to the other treatment groups.

DETAILED DESCRIPTION

Figure 1A:
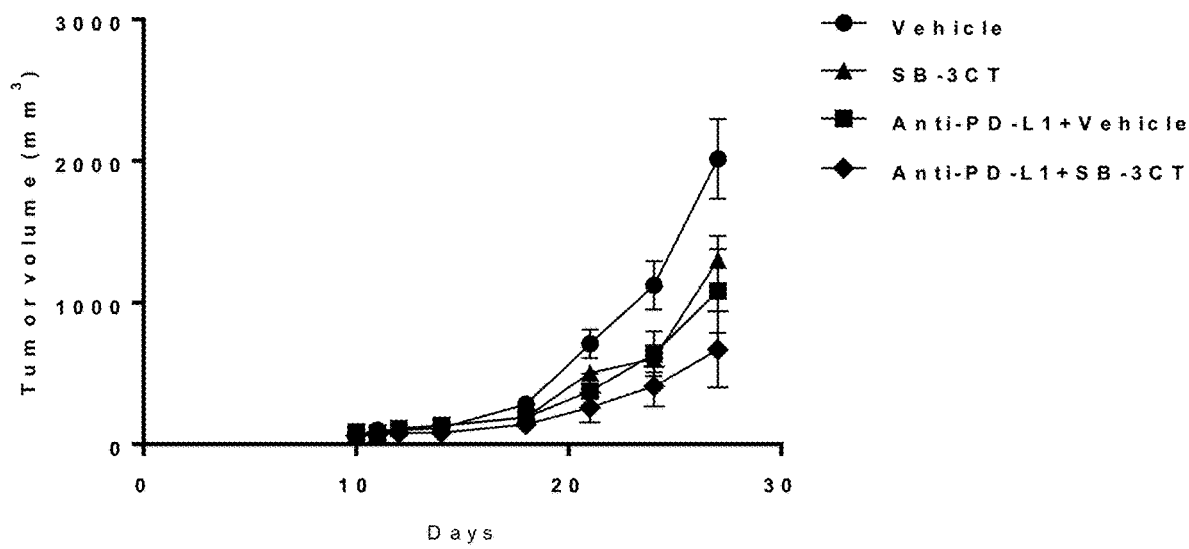
FIGS. 1A-1D show the effect of blocking MMP9 on primary tumor growth and survival in a mouse model of breast cancer.

Before describing the methods of the invention, it should be understood that this invention is not limited to the particular methodology and protocols as described herein. It is also to be understood that the terminology used herein is for the purpose of describing particular embodiments of the invention only and, if not defined otherwise, it is not intended to limit the scope of the present invention which will be recited in the appended claims.

It must also be noted that as used herein and in the appended claims, the singular forms "a", "an", and "the" include plural reference unless the context clearly dictates otherwise.

As used herein, the term "a cancer therapy" may be used interchangeably with the term "a "a cancer-modality therapy", and include plural reference, namely, one single modality therapy or a combination of two or more modality therapies.

As used herein, the terms "induced", "driven" and "generated" are used interchangeably to denote the factors induced into the circulation by the cancer patient in response to the cancer therapy ("host-response").

In cancer therapy, a cycle of treatment means that the drug is administered to the patient at one point in time (for example, injections over a day or two) and then there is some time (e.g., 1, 2 or 3 weeks) with no treatment. As used herein, "a session of treatment" refers to the "one point in time" when the ICI is administered to the patient at the beginning of a cycle of treatment. The treatment and rest time make up one "treatment cycle". When the patient gets to the end of the cycle, it starts again with the next cycle. A series of cycles of treatment is called "a course".

As used herein, the term "an immune checkpoint inhibitor (ICI)" refers to a single ICI, a combination of ICIs and a combination of an ICI with another cancer therapy. The ICI may be a monoclonal antibody, a humanized antibody, a fully human antibody, a fusion protein or a combination thereof.

In one aspect, the invention relates to a method of treating a cancer patient with an immune checkpoint inhibitor (ICI), the method comprising the steps of:
(i) performing an assay on a blood sample selected from blood plasma, whole blood, blood serum or peripheral blood mononuclear cells obtained from the cancer patient at a time point after a session of treatment with said ICI, to determine the levels of one or more of a plurality of host-driven resistance factors that are driven by the host ("the cancer patient") in response to treatment with the ICI, said one or more of the plurality of factors promoting in a personalized form responsiveness or non-responsiveness of the cancer patient to the treatment with the ICI;
(ii) obtaining reference levels for each of the one or more of the plurality of host-driven resistance factors of step (i) by determining the levels of each of said factors in a blood sample of the same type of the blood sample of step (i), obtained from the cancer patient at a time point before said session of treatment with the ICI;
(iii) establishing the fold change for each of the one or more of the plurality of the host-driven resistance factors of step (i) by comparing the level of each host-driven resistance factor of step (i) with the reference level of step (ii) for the same factor;
(iv) determining that the cancer patient has a favorable or a non-favorable response to the treatment with said ICI based on the fold change established in step (iii) for one or more of the plurality of host-driven resistance factors of step (i); and
(iva) if the cancer patient has a non-favorable response to the treatment with said ICI based on the fold change established in step (iii) for one or more of the plurality of the host-driven resistance factors, then selecting a dominant factor among the one or more host-driven resistance factors showing a fold change indicative of said non-favorable response, and treating the patient with a therapeutically effective amount of the ICI along with a therapeutically effective amount of an agent that blocks the activity of the selected dominant host-driven resistance factor (herein "the dominant factor"), or of the receptor thereof; or
(ivb) if the cancer patient has a favorable response to the treatment with said ICI based on the fold change established in (iii) for one or more of the plurality of host-driven resistance factors, then continuing the treatment of the cancer patient with the ICI alone.

A "favorable response" of the cancer patient indicates "responsiveness" of the cancer patient to the treatment with the ICI, namely, the treatment of the responsive cancer patient with the ICI will lead to the desired clinical outcome such as tumor regression, tumor shrinkage or tumor necrosis; an anti-tumor response by the immune system; preventing or delaying tumor recurrence tumor growth or tumor metastasis. In this case, it is possible to continue the treatment of the responsive cancer patient with the ICI alone, as defined in step (ivb) above.

A "non-favorable response" of the cancer patient indicates "non-responsiveness" of the cancer patient to the treatment with the ICI due to induction of host-driven resistance factors that may be pro-tumorigenic, e.g., pro-angiogenic, pro-inflammatory/chemotactic or proliferative growth factors, or pro-metastatic factors, and thus the treatment of the non-responsive cancer patient with the ICI will not lead to the desired clinical outcome but to non-desired outcomes such as tumor expansion, recurrence and metastases. In order to achieve the desired clinical outcome, it is necessary to blockade the dominant factor as defined above in step (iva) and treating the non-responsive cancer patient with a combination of the ICI and a therapeutic agent that blocks the activity of the selected dominant factor.

Thus, in one embodiment, the invention relates to a method for treatment of a cancer patient non-responsive to treatment with an immune checkpoint inhibitor (ICI), the method comprising administering to the cancer patient a therapeutically effective amount of the ICI along with a therapeutically effective amount of an agent that blocks the activity of a dominant factor, or of the receptor thereof, the dominant factor being selected among the plurality of host-driven resistance factors generated in response to treatment of the cancer patient with the ICI, the plurality of host-driven resistance factors having a fold-change predictive of a non-favorable response of the cancer patient to the treatment with the ICI, wherein the fold change is established by comparing: (i) the level of each host-driven resistance factors in a blood sample selected from blood plasma, whole blood, blood serum or peripheral blood mononuclear cells, obtained from the cancer patient after a session of treatment with the ICI, with (ii) a reference level obtained for the same factor from a blood sample of the same type of (i), obtained from the cancer patient before said session of treatment with the ICI.

In a preferred embodiment, the blood samples of steps (i) and (ii) are both blood plasma.

In certain embodiments of the invention, the session of treatment with the ICI is one of multiple sessions of treatment. In certain embodiments, the one of multiple sessions of treatment with the ICI is the first session of treatment with said ICI, the blood sample of step (i) is obtained from the cancer patient at about 20, 24, 30, 36, 40, 48, 50, 60, 72 hours or more, including up to one week or more, up to two weeks or more or up to three weeks or more, after said first session of treatment, and the reference blood sample of step (ii) is obtained from the cancer patient at a time point including at about 72 hours or less, including at about 60, 50, 48, 40, 36, 30, 24 or 20 hours or less or just before said first session of treatment with the ICI.

In certain embodiments, the one of multiple sessions of treatment of the cancer patient with the ICI is the first session of treatment, when the treatment with the ICI is started. In this case, the reference/baseline sample of step (ii), preferably blood plasma, is obtained from the cancer patient at a time point before starting the treatment including at about 72 hours or less, including at about 60, 50, 48, 40, 36, 30, 24 or 20 hours or just before said first session of treatment with the ICI. The comparison is then made between the concentration levels of the factors determined in the blood sample, preferably blood plasma, obtained from the cancer patient at about 20, 24, 30, 36, 40, 48, 50, 60, 72 hours or more, including up to one week or more, up to two weeks or more, or up to three weeks or more, after said first session of treatment with the ICI.

In certain other embodiments of the invention, the session of treatment of the cancer patient with the ICI is one of multiple sessions of treatment that is not the first session of treatment with the ICI. In this case, the blood sample is obtained from the cancer patient at any time point between two consecutive sessions of treatment with the ICI and serves simultaneously as the blood sample of step (i) and the reference blood sample according to step (ii) for the next session assay according to step (i). The time between two consecutive sessions of treatment depends on the treatment protocol approved for the specific ICI and may be, for example, of 2 or 3 weeks, depending on the ICI, and the blood sample may be obtained at day 1, 2, 3, 7, 14, or 21 days between two consecutive sessions.

In accordance with the invention, the levels of the plurality of factors generated by the host/cancer patient in response to the treatment with the immune checkpoint inhibitor are determined in the blood sample, preferably blood plasma, obtained from the patient after treatment with ICI. The value (factor concentration in pg/mL) obtained for each factor is then compared with a reference level, which is the baseline level of concentration of the same factor determined in a blood sample, preferably blood plasma, obtained previously from the same cancer patient (hereinafter "reference/baseline sample"). The change in the level of one or more of the factors identified in the blood sample obtained from the cancer patient after the treatment with the ICI compared to the reference/baseline level, is defined by the fold change for each factor. The fold change for each factor is determined by calculating the ratio of treatment:reference/baseline values for the factor.

The fold-change of each of the one or more of the plurality of the host-driven resistance factors is considered significant and predictive of a non-favorable response of the cancer patient to the treatment with the ICI if its value is about 1.5 or higher denoting an up-regulation of the factor, or the fold-change is considered significant and predictive of a favorable response of the cancer patient to the treatment with said ICI if its value is about 0.5 or lower denoting down-regulation of the factor.

In accordance with the invention, the prediction of a favorable or a non-favorable response of the cancer patient to the treatment with an ICI is based on significant fold changes of one or more, optionally two or more, three or more, four or more, five or more, six or more, seven or more, eight or more, nine or more, ten or more, eleven or more, twelve or more, thirteen or more, fourteen or more, fifteen or more, twenty or more, or twenty-five or more, of the host-driven resistance factors.

The factors/biomarkers induced into the circulation of the cancer patient in response to treatment with the ICI include molecular factors such as cytokines, chemokines, growth factors, enzymes and soluble receptors. The factors may be pro-tumorigenic or pro-metastatic factors. The pro-tumorigenic factors may be pro-angiogenic, pro-inflammatory/chemotactic or proliferative growth factors.

In certain embodiments, the session of treatment is the first session of a plurality of sessions of treatment of the cancer patient, when the treatment is started. In this case, the comparison is between the factors determined in the blood sample, preferably blood plasma, obtained from the cancer patient after first starting treatment with the ICI, and the same factors found in the reference/baseline blood sample, preferably blood plasma, obtained from the cancer patient before starting treatment with the ICI. The results may assist the medical oncologists treating the patient to decide if or how to continue the treatment of the cancer patient.

In certain embodiments, the method of the invention is performed for monitoring treatment response in a cancer patient being treated with an ICI. In this case, the session of treatment is one of the sessions of several sessions of treatment, but not the first one. The results will assist the medical oncologist in their decisions if or how to continue the treatment.

In certain embodiments, the fold change determined for pro-tumorigenic factors is predictive of the patient's favorable response to the cancer therapy and the decision may be to continue the treatment with the same ICI as scheduled.

In certain embodiments, the fold change determined for pro-tumorigenic factors is predictive of the patient's non-favorable response to the ICI. In this case, depending on the specific biological activity of the pro-tumorigenic factors, the decision may be to continue the treatment with the same ICI but with the addition of a drug that blocks the biological activity of the tumorigenic factors, for example, by adding to the treatment an anti-inflammatory drug if the factors are pro-inflammatory or by adding to the treatment an anti-angiogenic drug if the factors are pro-angiogenic.

Immune checkpoints are regulators of immune activation. They play a key role in maintaining immune homeostasis and preventing autoimmunity. In cancer, immune checkpoint mechanisms are often activated to suppress the nascent anti-tumor immune response. Immune checkpoint molecules are considered as good targets for cancer immunotherapy. Immune checkpoint inhibitors (ICI) that cause blockade of the immune checkpoint molecules are considered good candidates for the development of drugs for cancer immunotherapy with the potential for use in multiple types of cancers and are already in use or are under development.

Examples of immune checkpoints that are candidates as targets for development of immune checkpoint inhibitor (ICI) drugs include PD-1 (Programmed Death-1) that has two ligands, PD-L1 and PD-L2; CTLA-4 (Cytotoxic T-Lymphocyte-Associated protein 4); A2AR (Adenosine A2A receptor), also known as ADORA2A; BT-H3, also called CD276; BT-H4, also called VTCN1; BT-H5; BTLA (B and T Lymphocyte Attenuator), also called CD272; IDO (Indoleamine 2,3-dioxygenase); KIR (Killer-cell Immunoglobulin-like Receptor); LAG-3 (Lymphocyte Activation Gene-3); TDO (Tryptophan 2,3-dioxygenase); TIM-3 (T-cell Immunoglobulin domain and Mucin domain 3); VISTA (V-domain Ig suppressor of T cell activation).

In certain embodiments of the invention, the ICI is a monoclonal antibody (mAb) against PD-1 or PD-L1 that neutralizes/blocks the PD-1 pathway. In certain embodiments, the anti-PD-1 mAb is Pembrolizumab (Keytruda; formerly called lambrolizumab), approved or tested for treatment of advanced or unresectable melanoma, metastatic non-small cell lung cancer (NSCLC), renal cell carcinoma (RCC), and recurrent squamous cell carcinoma of the head and neck (SCCH). In certain embodiments, the anti-PD-1 mAb is Nivolumab (Opdivo), approved or tested for NSCLC, RCC, melanoma and colorectal cancer (CRC). In certain embodiments, the anti-PD-1 mAb is Pidilizumab (CT0011), approved or tested for non-Hodgkin's lymphoma, chronic lymphocytic leukemia, Hodgkin's lymphoma, multiple myeloma, and acute myeloid leukemia. In certain embodiments, the anti-PD-1 mAb is REGN2810, AMP-224, MEDI0680, or PDR001.

In certain other embodiments of the invention, the immune checkpoint inhibitor is a mAb against PD-L1. In certain embodiments, the anti-PD-L1 mAb is Atezolizumab (Tecentriq), Avelumab (Bavencio), or Durvalumab (Imfinzi), approved for multiple cancers. Atezolizumab is being tested in combination with one or two other cancer agents such as bevacizumab, gemcitabine, cisplatin, docetaxel, paclitaxel, vinflunine entinostat, daratumumab, MPDL3280A, carboplatin, Nab-paclitaxel, Radium-223 dichloride, obinutuzumab, for multiple cancers.

In certain other embodiments of the invention, the ICI is a mAb antibody against CTLA-4. In certain embodiments, the anti-CTLA-4 is Ipilimumab (Yervoy), approved or tested for advanced/metastatic melanoma and castrate-resistant prostate cancer. In certain other embodiments, the anti-CTLA-4 mAb is Tremelimumab (formerly ticilimumab).

In certain embodiments, the ICI is an inhibitor including: (i) anti-B7-H3, such as MGA271; (ii) anti-IDO, such as epacadostat; (iii) anti-KIR, such as Lirilumab; (iv) anti-LAG-3, such as Relatlimab (BMS-986016), LAG 525, REGN3767; (v) anti-TIM-3, such as TSR022 or MBG453; and (vi) anti-VISTA, such as JNJ 61610588.

In certain embodiments, a combination of two ICIs is used according to the invention. In certain embodiments, the combination comprises an anti-PD-1 and an anti-CTLA-4, e.g., Nivolumab-Ipilimumab and REGN2810-Ipilimumab. In certain embodiments, the combination comprises an anti-PD-L1 and an anti-CTLA-4, e.g., Durvalumab-Tremelimumab. In certain embodiments, the combination comprises an anti-PD-1 and an anti-PD-L1, e.g., Nivolumab-Atezolimumab. In certain embodiments, the combination comprises an anti-LAG-3 and an anti-PD-1, e.g., Relatlimab-Nivolumab or REGN3767-REGN2810. In certain embodiments, the combination comprises an anti-PD-1 and an MO inhibitor, e.g., Pembrolizurriab and Epacadostat and Nivolumab-Epacadostat.

Costimulatory molecules such as CD137 (4-1BB), CD134 (OX40), glucocorticoid-induced TNFR (GITR; CD357), and CD40 are expressed by activated T cells, activated natural killer (NK) cells, natural killer T (NKT) cells, Tregs, and other immune cells. The inhibition of the immune checkpoint PD-1 and stimulation of costimulatoiy molecules by agonist antibodies are complementary strategies to enhance immune responses and therefore provide a strong rationale for use in combination. Thus, in certain embodiments, the invention encompasses a combination of an ICI with an agonistic mAb against T-cell co-stimulatory molecules including an anti-ICOS mAb, e.g., MEDI-570 or BMS-986226; an anti-OX40 mAb e.g., MOXR0916, KHK4083, MEDI0562 or MEDI6469; an anti-CD40 mAb; and an anti-CD137 (4-IBB) mAb, e.g., Urelumab or Utomilumab.

In certain embodiments of the invention, the ICI is administered in combination with one or more conventional cancer therapy including chemotherapy, targeted cancer therapy and radiotherapy. Combinations of ICI and radiation therapy have been studied in multiple clinical trials.

In certain embodiments, the ICI is used in combination chemotherapy that may be with a single or a combination of chemotherapy drugs, or metronomic chemotherapy. The combinations Pembrolizumab+carboplatin+paclitaxel, Pembrolizumab+gemcitabine+docetaxel, Nivolumab+gemcitabine+cisplatin, Ipilimumab+carboplatin+paclitaxel, and other combinations were tested or are being tested in clinical trials.

In certain embodiments, the ICI therapy is used in combination with targeted cancer therapy, sometimes called "molecularly targeted therapy". In certain embodiments, the targeted therapy drugs are small molecules such as bortezomib (Velcade), sunitinib (Sutent). In certain embodiments, the targeted therapy drugs are monoclonal antibodies such as bevacizumab (Avastin), panitumumab (Vectibix), daratumumab (Darzalex). In certain embodiments, an anti-PD-1 is used in combination with sunitinib (Sutent) or pazopanib (Votrient) that was tested for treatment of RCC, or a combination of anti-CTLA-4 ipilimumab with BRAF inhibitor dabrafenib (Tafinlar).

In certain embodiments, the ICI therapy is used in combination with anti-angiogenic therapy, for example, with a mAb that targets VEGF. Thus, the combination may be of Ipilimumab and bevacizumab.

In certain embodiments, the ICI therapy is used in combination with other immunotherapies such as cancer vaccines, immunomodulators, immunostimulatory cytokines, e.g., GM-CSF, IFN-α, TGF-β, IL-10, IL-2, IL-15, IL-1.8, and IL-21, or oncolytic viruses. In certain embodiments, anti-CTLA-4 ipilimumab or anti-PD-1 pembrolizumab is used in combination with oncolytic virus talimogene laherparepvec (I-VIE).

In accordance with the invention, the cancer therapy is related to all types of cancer, primary or metastatic, in all stages of the disease, including, but without being limited to, a primary or a metastatic cancer including bladder, bone, breast, brain, cervical, colon, colorectal, esophageal, gastric cancer, gastrointestinal, glioblastoma, head and neck, head and neck squamous cell cancer, hepatocellular cancer, kidney, liver, lung including small cell lung cancer and non-small cell lung cancer (NSCLC), melanoma, nasopharyngeal, ovarian, pancreas, penile, prostate, skin, testicular, thymus, thyroid, urogenital, or uterine cancer, leukemia, lymphoma, multiple myeloma and sarcoma.

In certain embodiments, the cancer is leukemia, a cancer of the body's blood-forming tissues, including the bone marrow and the lymphatic system. In certain embodiments, the leukemia is selected from acute lymphocytic leukemia (ALL), acute myeloid leukemia (AML), chronic lymphocytic leukemia (CLL) or chronic myeloid leukemia (CML). In certain embodiments, the cancer is multiple myeloma.

In certain embodiments, the cancer is non-small cell lung cancer (NSCLC). In certain embodiments, the cancer is advanced (stage III or IV) or metastatic NSCLC.

In certain embodiments the cancer is metastatic melanoma, renal-cell carcinoma (RCC), classic Hodgkin's lymphoma (HL), bladder carcinoma, Merkel cell carcinoma, head and neck cancer, or solid tumors with mismatch repair-deficiency The host-driven factors/biomarkers identified by the method of the invention after administration of an immune checkpoint inhibitor to a cancer patient are specific to: (i) the cancer patient; and (ii) the immune checkpoint inhibitor. This is the "host response" that provides specific information about the cancer patient and allows the prediction in a personalized form to help diagnose, plan treatment, find out how well treatment is working, or make a prognosis If the treatment is with one single ICI, the factors generated by the host/patient are specific to this particular ICI. If the treatment is carried out with a combination of two ICIs, the factors generated by the host/patient are specific to this combination of ICIs. If treatment is with the ICI in combination with another cancer therapy, the factors generated by the host/patient are specific to this combination.

In certain embodiments, the biomarkers are molecular factors such as cytokines, chemokines, growth factors, enzymes or soluble receptors. Some of these factors induce cells that affect the tumor and contribute to tumor angiogenesis and cancer re-growth, thereby promoting resistance to the therapy used. Examples of such cells include bone-marrow derived cells (BMDCs) that are mobilized from the bone-marrow compartment by cytokines and growth factors such as G-CSF and SDF-1α, and subsequently colonize the treated tumors and promote cancer therapy resistance, particularly, but not exclusively, chemotherapy resistance. Other cells are immune cells such as macrophages and antigen-presenting cells, or stromal cells within the tumor microenvironment which play a pivotal role in tumor progression.

The host-mediated cellular and molecular mechanisms that contribute to tumor resistance to a cancer therapy are based on the biological functions of the factors and/or cells generated in the host by the particular cancer therapy. Each factor may exhibit one or more biological functions or activities.

In certain embodiments, the factors are tumorigenic and contribute to tumor growth. In certain embodiments, the tumorigenic factors are pro-angiogenic. In other embodiments, the tumorigenic factors are pro-inflammatory/chemotactic. In yet other embodiments, the tumorigenic factors are proliferative growth factors.

In certain embodiments, the pro-angiogenic factors include, without being limited to, ANG (angiogenin); angiopoietin-1; angiopoietin-2; bNGF (basic nerve growth factor); cathepsin S; Galectin-7; GCP-2 (granulocyte chemotactic protein, CXCL6); G-CSF (granulocyte-colony stimulating factor); GM-CSF (granulocyte-macrophage colony stimulating factor, also known as colony-stimulating factor 2, CSF2); PAI-1 (plasminogen activator Inhibitor-1); PDGF (platelet-derived growth factor) selected from PDGF-AA, PDGF-BB, PDGF-AB; P1GF (or PLGF, placental growth factor); P1GF-2; SCF (stem-cell factor); SDF-1 (CXCL12, stromal cell-derived factor-1); Tie2 (or TIE-2, an endothelial receptor tyrosine kinase); VEGF (vascular endothelial growth factor) selected from VEGF-A, VEGF-C and VEGF-D; VEGF-R1; VEGF-R2; VEGF-R3.

In certain embodiments, the pro-inflammatory and/or chemotactic factors include, without being limited to, 6Ckine (CCL21, Exodus-2); angiopoietin-1; angiopoietin-2; BLC (CXCL13, B lymphocyte chemoattractant or B cell-attracting chemokine 1 (BCA-1); BRAK (CXCL14); CD186 (CXCR6); ENA-78 (CXCL5, Epithelial cell derived neutrophil activating peptide 78,); Eotaxin-1 (CCL11); Eotaxin-2 (CCL24); Eotaxin-3 (CCL26); EpCAM (Epithelial cell adhesion molecule); GDF-15 (growth differentiation factor 15, also known as macrophage inhibitory cytokine-1, MIC-1); GM-CSF; GRO (growth-regulated oncogene); HCC-4 (CCL16, human CC chemokine 4); I-309 (CCL1); IFN-γ; IL-1α; IL-1β; IL-1R4 (ST2); IL-2; IL-2R; IL-3; IL-3Rα; IL-5; IL-6; IL-6R; IL-7; IL-8; IL-8 RB (CXCR2, interleukin 8 receptor, beta); IL-11; IL-12; IL-12p40; IL-12p70; IL-13; IL-13 R1; IL-13R2; IL-15; IL-15Rα; IL-16; IL-17; IL-17C; IL-17E; IL-17F; IL-17R; IL-18; IL-18BPa; IL-18 Rα; IL-20; IL-23; IL-27; IL-28; IL-31; IL-33; IP-10 (CXCL10, interferon gamma-inducible protein 10); I-TAC (CXCL11, Interferon-inducible T-cell alpha chemoattractant); LIF (Leukemia inhibitory factor); LIX (CXCL5, lypopolysaccharide-induced CXC chemokine); LRP6 (low-density lipoprotein (LDL) receptor-related protein-6); MadCAM-1 (mucosal addressin cell adhesion molecule 1); MCP-1(CCL2, monocyte chemotactic protein 1); MCP-2 (CCL8); MCP-3 (CCL7); MCP-4 (CCL13); M-CSF (macrophage colony-stimulating factor, also known as colony stimulating factor 1 (CSF1); MIF (macrophage migration inhibitory factor); MIG (XCL9, Monokine induced by gamma interferon); MIP-1 gamma (CCL9, macrophage inflammatory protein-1 gamma); MIP-1α (CCL3); MIP-1β; MIP-1δ (CCL15); MIP-3α (CCL20); MIP-3β (CCL19); (CCL23, Myeloid progenitor inhibitory factor 1); PARC (CCL18, pulmonary and activation-regulated chemokine); PF4 (CXCL4, platelet factor 4); RANTES (CCL5, regulated on activation, normal T cell expressed and secreted); Resistin; SCF; SCYB16 (CXCL16, small inducible cytokine B16); TACI (transmembrane activator and CAML interactor); TARC (CCL17, CC thymus and activation related chemokine); TSLP (Thymic stromal lymphopoietin); TNF-α (tumor necrosis factor-α); TNF R1; TRAIL-R4 (TNF-Related Apoptosis-Inducing Ligand Receptor 4); TREM-1 (Triggering Receptor Expressed On Myeloid Cells 1).

In certain embodiments, the proliferative factors include, without being limited to, Activin A; Amphiregulin; Axl (AXL, a receptor tyrosine kinase); BDNF (Brain-derived neurotrophic factor); BMP4 (bone morphogenetic protein 4); cathepsin S; EGF (epidermal growth factor); FGF-1 (fibroblast growth factor 1); FGF-2 (also known as bFGF, basic FGF); FGF-7; FGF-21; Follistatin (FST); Galectin-7; Gas6 (growth arrest-specific gene 6); GDF-15; HB-EGF (heparin-binding EGF); HGF; IGFBP-1 (Insulin-like growth factor binding protein-1); IGFBP-3; LAP (Latency-associated peptide); NGF R (nerve growth factor receptor); NrCAM (neuronal cell adhesion molecule); NT-3 (neurotrophin-3); NT-4; PAI-1; TGF-α (transforming growth factor-α); TGF-β; and TGF-β3; TRAIL-R4 (TNF-Related Apoptosis-Inducing Ligand Receptor 4).

In certain embodiments, the pro-metastatic factors include, without being limited to, ADAMTS1 (A disintegrin and metalloproteinase with thrombospondin motifs 1); cathepsin S; FGF-2; Follistatin (FST); Galectin-7; GCP-2; GDF-15; IGFBP-6; LIF; MMP-9 (Matrix metallopeptidase 9, also known as 92 kDa gelatinase or gelatinase B (GELB); pro-MMP9; RANTES (CCL5); SDF-1 (stromal cell-derived factor-1, also known as CXCL12) and its receptor CXCR4.

The factors may also be anti-tumorigenic factors, e.g., anti-angiogenic, anti-inflammatory and/or anti-proliferative growth factors.

In certain embodiments, the circulating factors indicating a host response to ICI include, but are not limited to, ADAMTS1, amphiregulin; Axl; CCL5/RANTES; CCL17/TARC; EGF; Eotaxin-2; FGF-21; Gas6; G-CSF; GM-CSF; HGF; IFN-gamma; IL-1Ralpha; IL-2; IL-6; IL-7; IL-10; IL-12p40; IL-13; IL-33; I-TAC; MadCAM-1; MCP-5; TACI; M-CSF; MMP-9; PDGF-BB; pro-MMP9; SCF.

In accordance with the present invention, many of the factors that were upregulated in response to anti-PD-1 treatment are key players in pro-tumorigenic and pro-metastatic processes such as angiogenesis, inflammation, chemotaxis and proliferation. Upregulated pro-angiogenic factors include: G-CSF; GM-CSF; and PDGF-BB. Up-regulated pro-inflammatory and/or chemotactic factors include: CCL17/TARC; CCL5/RANTES; G-CSF; GM-CSF; IFN-gamma; IL-1Ralpha; IL-2; IL-6; IL-7; IL-10; IL-12p40; IL-13; IL-33; and M-CSF. Upregulated proliferative growth factors include: FGF-21; Gash; and HGF. Upregulated pro-metastatic factors include: MMP-9.

In accordance with the present invention, many of the factors that were upregulated in response to anti-PD-L1 treatment are key players in pro-tumorigenic and pro-metastatic processes such as inflammation, chemotaxis and proliferation. Upregulated pro-angiogenic factors include: G-CSF; and SCF. Upregulated pro-inflammatory and/or chemotactic factors include: Eotaxin-2; G-CSF; IL-1ra; IL-6; IL-7; IL-33; I-TAC; MadCAM-1; MCP-5; SCF; and TACI. Upregulated proliferative growth factors include: amphiregulin; Axl; EGF; and HGF. Upregulated pro-metastatic factors include: ADAMT S1 and pro-MMP9.

As used herein, the term "dominant factor" denotes a potent factor that may be upstream of a signaling pathway that affects a biological process that is vital for the living cell and living organism. These biological processes include proliferation, inflammation, metastasis, and others, and are made of several signaling pathways ultimately leading to activation or inhibition of the biological process. A "signaling pathway" is a row of events in which proteins in the same pathway transfer signal to each other. After the first protein in a pathway receives a signal, it activates another protein which activates another protein and so forth, ultimately leading to activation of one or more cell functions.

A "dominant factor" may also be a key factor that highly interacts with, and highly affects, many other factors/proteins. According to the invention, the dominant factors are selected based on an algorithm which identifies the protein-protein interactions of factors based on the literature. When a factor has more interactions, it serves as a hub and therefore it is a dominant factor. The term "protein-protein interactions" refers to physical interactions or cross-talk between two or more proteins, resulting in activation or inhibition of signal transduction or protein activity. The term "protein hubs" refers to highly connected proteins that play central and essential role in biological processes and thus may confer the host with resistance, limit or counteract the effectiveness of the treatment of the cancer patient with the cancer therapy modality.

The terms "block", "neutralize" or "inhibit" are herein used interchangeably and refer to the capability of an agent of preventing the selected dominant factor from exerting its function/biological activity.

Examples of dominant factors include, without limitation, Amphiregulin, EGF, EGFR, FGF, IFN-γ, IL-1β, IL-2, IL-6, MMP-9, PDGF, TNF-α and VEGF-A.

To illustrate their qualifications as dominant factors, the properties of some of these factors is provided herein. Interleukin-1β (IL-1β, IL-1b) is a cytokine member of the IL-1 family, produced by different immune cells including macrophages. It is a potent mediator of the inflammatory response and also known to be involved in several biological processes such as cell proliferation and apoptosis, as well as cell differentiation. IL-1b was mostly investigated as a protein that initiates the pro-inflammatory cascade. It physically interacts with enzymes such as CASP1, IL1RA, IL1R1, CMA1, IL1RB, IL1A, IL1R2; genetically interacts with MAPK8IP2, ZNF675 and UBEN2N; and is co-expressed with A2M, CXCL8, IL18, CAASp1, IL1R1 and others. Thus, IL-1b serves as a hub for interactions with a large number of proteins that affect several biological pathways including cell proliferation, apoptosis and differentiation as well as inflammation and angiogenesis.

Another dominant factor is Interleukin-6 (IL-6), which is a cytokine that acts mainly as a pro-inflammatory factor but also sometimes as an anti-inflammatory factor produced by muscle cells and as a result downregulate a number of pro-inflammatory proteins such as IL-1, IL-10 and TNF-α. IL-6 is involved in a number of biological processes including bone formation, disruption of blood brain barrier, macrophage activation and innate immune system contribution, stimulates the synthesis of neutrophils and B cells, and is also involved in neurological activities such as disorders, stress and depression. IL6 interacts and affects a large number of proteins: it physically interacts with HRH1, OSM, IL6ST, IL6R and ZBTB16, and was found to be co-expressed with a large number of proteins such as PTPRE, CSF3, CCL2, CXCL8, CXCL3, ICAM1 SELE, NFKBIZ among others. IL6 is involved in a number of pathways mediated by proteins such as LRPPRC, OSM, PTPRE, PIAS1 and IL6R. As such, IL6 serves as a dominant factor for a number of biological processes involved in immune cell activity, cell genesis, and cell-cell interactions.

A further dominant factor, vascular endothelial growth factor A (VEGF-A), is a growth factor that stimulates the formation of new blood vessels. It is involved in both angiogenesis (endothelial cell proliferation) as well as vasculogenesis (bone marrow-derived endothelial cell precursors and their differentiation). VEGF is important for embryonic cell development and neuronal development in the fetus, and is involved in leukocyte proliferation and differentiation, inflammation and several diseases such as age-related macular degeneration and the majority of cancers. VEGF-A physically interacts with a large number of proteins such as NRP1, NRP2, KDR, FLT1, PGF, THBS1, SPARC, GCP1 and VEGFC; it is co-expressed with SEMA3F, SHB, THBS1, FLT1 and VEGFC; it is involved with proteins of various pathways including PGF, CD2AP, IQGAP1, NEDD4; and it affects a number of biological processes such as angiogenesis, tumorigenesis, cell viability, proliferation and differentiation. As such, VEGF-A is considered a dominant factor, and vital factor for various biological processes both in normal physiological conditions as well as in disease states.

In certain embodiments, the selected dominant factor shows a fold change of ≥1.5 indicative of a non-favorable response of the cancer patient to the treatment with the ICI, and the treatment of the patient with said ICI may proceed in combination with an agent that blocks said dominant factor or the receptor thereof.

In certain embodiments, the dominant factor is selected from factors including amphiregulin, EGF, EGFR, FGF, IFN-γ, IL-1β, IL-2, IL-6, MMP9, PDGF, TNF-α and VEGF-A.

In certain embodiments, the dominant factor is MMP9, the ICI is an anti-PD-1 or anti-PD-L1 monoclonal antibody, and the cancer patient is treated with the ICI in combination with a MMP-9 inhibitor including SB-3CT.

In certain embodiments, the dominant factor is amphiregulin, the ICI is an anti-PD-1 or anti-PD-L1 monoclonal antibody, and the cancer patient is treated with the ICI in combination with an anti-amphiregulin antibody.

The invention will now be illustrated by the following non-limiting Examples.

EXAMPLES

Introduction

As discussed hereinbefore, recent clinical studies report that patients may sometimes develop resistance to ICIs, or may not respond to ICI therapy (Sharma et al., 2017). We describe herein that the cancer patient, i.e., the host, generates pro-tumorigenic factors in response to ICI therapy, which in turn contribute to tumor re-growth, progression and resistance to therapy. In order to identify the factors that contribute to this mechanism, we perform our in vivo experiments in both non-tumor- and tumor-bearing immunocompetent mice. This approach allows us to distinguish between the therapeutic anti-tumor activity of ICIs and the effect of these drugs on host cells. We focus on ICIs that are extensively used in the clinic, including anti-PD1, anti-PD-L1 and anti-CTL-4 monoclonal antibodies, and use murine tumor models that are known to be responsive or resistant to specific ICIs. For example, CT26 colon and EMT-6 breast carcinoma cell lines respond to anti-CTLA-4 and anti-PD-L1, respectively (Duraiswamy et al., 2013; Swart et a., 2013), whereas MC38 colon and 4T1 breast carcinoma cell lines are resistant or only modestly responsive to some ICIs (including anti-PD-1) (De Henau et al., 2016; Kodumudi et al., 2016), as also tested in our laboratory (not shown).

Materials and Methods

Materials

The following antibodies were purchased from BioXCell, West Lebanon, NH, USA: InVivoMAb anti-mouse-CTLA-4 (cat. #BE0131); InVivoMAb anti-mouse-IL-6 (cat. #BE0046); InVivoMAb anti-mouse-PD-1 (cat. #BE0146); InVivoPlus anti-mouse-PD-L1 (cat. #BE0101); and InVivoMAb Isotype control IgG2b antibody (cat. #BE0090). SB-3CT (IUPAC name: 2-(((4-phenoxyphenyl) sulfonyl) methyl)thiirane) was purchased from MedKoo Biosciences Inc (cat. #406563). Anti-amphiregulin (cat. #AF989) was purchased from R&D systems. A 10 mM stock solution of SB-3CT was prepared in 100% DMSO (Sigma). For in-vivo experiment, the stock solution was diluted to a final concentration of 1.25 mg/ml in 10% DMSO in normal saline.

(i) Cancer Cell Culture:

Murine EMT6 breast carcinoma and CT26 murine colon carcinoma cells were purchased from the American Type Culture Collection (ATCC, USA). The cells were used in culture for no more than 4 months after being thawed from authentic stocks and were regularly tested and found to be mycoplasma-free (EZ-PCR mycoplasma test kit, Biological Industries, Israel). EMT6 Cells were cultured in Dulbecco's modified eagle medium (DMEM) and CT26 cells were cultured in RPMI 1640 medium, both supplemented with 10% fetal bovine serum (FBS), 1% L-glutamine, 1% sodium-pyruvate and 1% penicillin-streptomycin (Biological Industries, Israel). Cells were cultured at 37° C. in 5% $CO_2$.

(ii) Animal Treatment Protocols and Tumor Models:

Naïve 8-10 week old female BALB/c, SCID or NOD-SCID mice (Harlan, Israel) were used in this study. Experiments were performed in accordance with the Animal Ethic Committee at the Technion (Haifa, Israel). The mice were intraperitoneally injected with anti-PD-1 or irrelevant IgG rat-anti-mouse antibodies (BioXCell, West Lebanon, NH, USA).

In other experiments, nave 8-10-week old female and male BALB/c or C57bl/6 mice (Harlan, Israel) were intraperitoneally injected with anti-PD-L1 or irrelevant IgG rat-anti-mouse antibodies (BioXCell, West Lebanon, NH, USA). In all cases, antibodies were administered at a dose of 200 µg/20 gr mouse, every other day over the period of 1 week (3 injections in total).

To investigate whether inhibiting host-derived IL-6 improves the efficacy of anti-CTLA-4 treatment, EMT6 murine breast carcinoma cells ($5 \times 10^5$) were orthotopically implanted into the mammary fat pad of 8-10-week old BALB/c mice. Tumor size was assessed regularly with Vernier calipers using the formula width$^2 \times$length$\times 0.5$. In some experiments, mice were injected through the tail vein with EMT6 cells ($25 \times 10^3$) to form experimental lung metastasis. Mouse survival was monitored daily. When tumors reached a size of 140 mm$^3$, mice (n=5) were intraperitoneally (IP) injected with 200 µg anti-CTLA-4, 200 µg anti-IL-6 or a combination of the two antibodies once every three days (a total of 7 injections). Control mice (n=8) were left untreated. Tumors growth was monitored regularly and when tumor size reached 1500 mm$^3$, mice were sacrificed To investigate whether inhibiting host-derived MMP-9 improves the efficacy of anti-PD-L1 therapy, $0.5 \times 10^6$ EMT6 GFP murine breast carcinoma cells (a highly selective metastatic clone, called EMT6-F2, previously described for other cell line in Munoz et al., 2006) were orthotopically implanted in the mammary fat pad of 8-weeks old female BALB/c mice (n=7). When tumors reached a size of 100 mm$^3$, mice were IP injected with 200 µg anti-PD-L1, 50 µg SB-3CT (a MMP-2/MMP-9 selective inhibitor) (Kruger A., 2005, Bonfil R D., 2006); or a combination of anti-PD-L1 and SB-3CT. Control mice or mice treated with anti-PD-L1 monotherapy were injected with vehicle control (25% DMSO/65% PEG-200/10% PBS). Tumor growth and mouse survival were monitored and at endpoint (when tumors reached a size of 1500 mm$^3$, or maximum at day 27), mice were sacrificed.

To determine whether inhibiting host-derived amphiregulin improves the efficacy of anti-PD-L1 therapy, $2 \times 10^6$ CT26 cells were subcutaneously implanted in the right flank of 8-10 weeks old BALB/c mice. When tumors reached a size of 50 mm$^3$, mice were IP injected with 200 µg anti-PD-L1, 5 µg anti-AREG (as previously demonstrated in Fujiu K., 2017) or a combination of anti-PD-L1 and anti-AREG, every 3 days. Control mice were left untreated. Tumor growth and mouse survival were monitored.

(iii) IL-6 Quantification by ELISA:

Seven weeks old naïve female BALB/c mice (n=4) were intraperitoneally injected every three days for a total of 3 injections with 200 μg anti-PD-L1 or anti-CTLA-4. Control mice (n=4) were left untreated. One day after the last injection, mice were sacrificed, and blood was collected into EDTA-coated tubes by cardiac puncture. Plasma was isolated by centrifugation of the whole blood at 1300 g for 10 min. at room temperature. Supernatants (representing the plasma layer) were collected and the level of IL-6 was determined by ELISA (IL-6 mouse ELISA Kit, 100712 Abcam) according to the manufacturer's instruction.

(iv) Plasma Samples and Conditioned Medium Preparation:

Blood from control IgG-, anti-PD-1-, or anti-PD-L1-treated mice was collected into EDTA-coated tubes by cardiac puncture. Subsequently, plasma was isolated by centrifugation of whole blood at 1000 g, 4° C., for 20 min. Plasma was stored in aliquots at −80° C. until further use. Bone marrow derived cells were flushed from the femurs of IgG or anti-PD-1 treated mice. Bone marrow cells (1×10$^6$ cells/ml) were cultured in serum-free DMEM for 24 hours to generate conditioned medium (CM).

(v) Antibody Arrays:

Three protein profiling experiments were performed. In the first experiment, plasma samples extracted from IgG- or anti-PD-1 treated female BALB/c mice were pooled per treatment group (n=5 per group). Samples were applied to a membrane-based Proteome Profiler Mouse XL Cytokine Array (R&D Systems; Cat no: ARY028) according to the manufacturer's instruction to screen a total of 111 factors. In the second experiment, plasma samples extracted from IgG- or anti-PD-L1 treated female or male BALB/c or C57bl/6 mice were pooled per group (n=7 per group). Samples were applied to a glass slide-based Quantibody Mouse Cytokine Array (RayBiotech, Cat no: QAM-CAA-4000) according to the manufacturer's instruction to screen a total of 200 factors. In the third experiment, plasma samples extracted from IgG- or anti-PD-1 treated female BALB/c or SCID mice were pooled per group (n=7 per group). Samples were applied to a glass slide-based Quantibody Mouse Cytokine Array (RayBiotech, Cat no: QAM-CAA-4000) according to the manufacturer's instruction to screen a total of 200 factors. For the membrane-based array, pixel densities on developed X-ray films were analyzed using transmission mode densitometer and image analysis software. For the glass slide-based arrays, the fluorescent readout was detected by a laser fluorescent scanner. In all cases, data was normalized and the fold changes for each factor on the arrays were determined by calculating the ratio of treated: control values.

(vi) Statistical Analysis:

Data are expressed as mean±standard deviation (SD). The statistical significance of differences was assessed by one-way ANOVA, followed by Tukey ad hoc statistical test using GraphPad Prism 5 software (La Jolla, CA). Student t-test was used in some experiments when comparing only two groups. Differences between all groups were compared with each other. For the IL-6 quantification by ELISA, the statistical significance of differences was assessed by two tailed unpaired T-test. For tumor growth experiments, statistical significance is assessed by multiple T-test. For survival analysis, differences are assessed by Log-rank Mantle-Cox. Differences were considered significant at p values below 0.05.

Example 1. The Effect of Immune Checkpoint Inhibitor Therapy on Circulating Host-Derived Factors—a Protein Profiling Approach in Mice Previous experiments suggest that anti-PD-1 therapy induces an upregulation of factors in the circulation which ultimately promotes tumor cell aggressiveness. Such effects may occur in response to other types of immune checkpoint inhibitor therapies. To identify host-derived circulating factors whose levels change in response to anti-PD-1 and anti-PD-L1 therapies, we performed 3 protein array-based screens using naïve (non-tumor bearing) mice. The use of naïve mice allows us to identify factors specifically generated by the host in response to therapy, independent of the tumor.

In the first screen, naïve 8-10 week old female BALB/c mice (n=3) were intraperitoneally injected with anti-PD-1 rat anti-mouse antibody (BioXCell, West Lebanon, NH, USA) at a dose of 200 μg/20 gr mouse every other day over a period of 1 week (3 injections in total). Control mice (n=3) were similarly injected with a rat-anti-mouse IgG antibody at the same dose. One week after the first injection, mice were sacrificed, and blood was collected into EDTA-coated tubes by cardiac puncture. Plasma was isolated by centrifugation of whole blood at 1300 g for 10 min. at room temperature. Supernatants (representing the plasma samples) were collected and pooled per group. Aliquots were stored at −80° C. until further use. Plasma samples were applied to a membrane-based Proteome Profiler Mouse XL Cytokine Array (R&D Systems; Cat no: ARY028) to screen a total of 111 factors. A full list of cytokines, enzymes and growth factors detected by the array is shown in Table 1. Pixel densities on developed X-ray films were analyzed using transmission mode densitometer and image analysis software. Normalized data was analyzed to identify factors whose circulating levels were changed in response to anti-PD-1 treatment. Specifically, the fold change was determined for each factor by calculating the ratio of treatment: control values. Factors exhibiting a fold change of more than 1.5 or less than 0.5 were defined as being up- or down-regulated, respectively, in response to anti-PD-1 treatment. These factors and their respective fold changes are listed in Table 2. Many of the factors that were upregulated in response to anti-PD-1 treatment are key players in pro-tumorigenic and pro-metastatic processes such as angiogenesis, inflammation, chemotaxis and proliferation. Upregulated pro-angiogenic factors include: G-CSF; GM-CSF; and PDGF-BB. Up-regulated pro-inflammatory and/or chemotactic factors include: CCL17/TARC; CCL5/RANTES; G-CSF; GM-CSF; IFN-gamma; IL-1Ralpha; IL-2; IL-6; IL-7; IL-10; IL-12p40; IL-13; IL-33; and M-CSF. Upregulated proliferative growth factors include: FGF-21; Gash; and HGF. Upregulated pro-metastatic factors include: MMP-9.

In the second screen, nave 8-10 week old female BALB/c, male BALB/c, female C57Bl/6 or male C57Bl/6 mice (n=7 mice per group) were intra-peritoneally injected with anti-PD-L1 or control IgG antibodies (BioXCell, West Lebanon, NH, USA) every other day over a period of 1 week (3 injections in total) at a dose of 200m/20 gr mouse per injection. Twenty-four hours after the last administration, mice were sacrificed, blood was drawn and plasma was prepared. Plasma samples from each group were pooled and applied to a glass slide-based Quantibody Mouse Cytokine Array (RayBiotech, Cat no: QAM-CAA-4000) according to the manufacturer's instruction to screen a total of 200 factors. A full list of cytokines, enzymes and growth factors detected by the array is shown in Table 3. The fold changes were determined for each factor on the protein array by calculating the ratio of treated: control values. Factors exhibiting a fold change of more than 1.5 or less than 0.5 were defined as being up- or down-regulated, respectively, in response to anti-PD-L1 treatment. These factors, and their respective fold changes are listed in Table 4. The data demonstrate that the profiles of up- and down-regulated factors do not completely overlap when comparing between the different mouse strains or when comparing between males and females of the same strain. This suggests that the response to anti-PD-L1 treatment is genotype-dependent. This may reflect differences known to exist also among cancer patients, and therefore provides a rationale for testing the response of the host in patients in a personalized manner. Many of the factors that were upregulated in response to anti-PD-L1 treatment are key players in pro-tumorigenic and pro-metastatic processes such as inflammation, chemotaxis and proliferation. Upregulated pro-angiogenic factors include: G-CSF; and SCF. Upregulated pro-inflammatory and/or chemotactic factors include: Eotaxin-2; G-CSF; IL-1ra; IL-6; IL-7; IL-33; I-TAC; MadCAM-1; MCP-5; SCF; and TACI. Upregulated proliferative growth factors include: amphiregulin; Axl; EGF; and HGF. Upregulated pro-metastatic factors include: ADAMTS1 and pro-MMP9.

To gain insight into which host cell types secrete these pro-tumorigenic factors, we performed a similar screen, comparing between BALB/c and SCID mice treated with anti-PD-1 or control IgG antibodies. SCID mice carry the severe combined immune deficiency (SCID) mutation on the BALB/c background, and therefore lack functional adaptive immune cell types (B cells and T cells). Naïve 8-10 week old female BALB/c or SCID mice (n=7 mice per group) were intraperitoneally injected with anti-PD-1 or control IgG antibodies (BioXCell, West Lebanon, NH, USA) every other day over a period of 1 week (3 injections in total) at a dose of 200m/20 gr mouse per injection. Twenty-four hours after the last administration, mice were sacrificed, blood was drawn and plasma was prepared. Plasma samples from each group were pooled and applied to a glass slide-based Quantibody Mouse Cytokine Array (RayBiotech, Cat no: QAM-CAA-4000) according to the manufacturer's instruction to screen a total of 200 factors. A full list of cytokines, enzymes and growth factors detected by the array is shown in Table 3. The fold changes were determined for each factor on the protein array by calculating the ratio of treated: control values. Factors exhibiting a fold change of more than 1.5 or less than 0.5 were defined as being up- or down-regulated, respectively, in response to anti-PD-1 treatment. These factors, and their respective fold changes are listed in Table 5. Several factors were found to be up-regulated in response to anti-PD-1 treatment, some of which were specific to BALB/c and not SCID mice, e.g., ADAMTS1; amphiregulin, I-TAC and SCF. These results suggest that these specific factors are secreted by cells of the adaptive immune system in response to anti-PD-1 treatment.

Collectively, these results demonstrate that anti-PD-1 and anti-PD-L1 treatments induce a response in the host that supports tumor progression, counteracting the desired therapeutic effects of immune checkpoint inhibitor therapy.

Example 2. The Effect of Reducing Host-Derived MMP-9 Levels on ICI Therapy in a Primary Breast Tumor Model Matrix metallopeptidase 9 (MMP9) is an enzyme that belongs to the zinc-metalloproteinases family involved in the degradation of the extracellular matrix. MMP-9 is involved in a variety of biological processes, among them are pro-tumorigenic and tissue regeneration biological processes, including epithelial to mesenchymal transition, cell proliferation, angiogenesis, bone formation and wound healing. MMP-9 is one of the key factors involved in invasion and metastasis. Due to its involvement in various key dominant biological pathways in cancer, for which drugs have been developed as anti-cancer agents, MMP-9 serves as a dominant factor induced in response to ICI therapy, and whose inhibition may improve therapeutic outcome.

MMP-9 was found to be induced in BALB/c mice following treatment with anti-PD-1 or anti-PD-L1, which demonstrate that: i) MMP-9 is secreted by bone marrow-derived cells of naïve BALB/c mice in response to anti-PD-1 treatment; ii) the plasma level of MMP9 is increased 5.4 fold in response to anti-PD-1 treatment in naïve BALB/c mice (Table 2); and iii) the plasma level of pro-MMP-9 is increased by 2-3 fold in response to anti-PD-L1 treatment in naïve BALB/c mice (Table 4). To investigate whether inhibiting host-derived MMP9 improves the efficacy of anti-PD-1 or anti-PD-L1 therapy, the MMP2/MMP9 selective inhibitor SB-3CT is used in combination with anti-PD-1 or anti-PD-L1 antibodies. EMT6 murine breast carcinoma cells ($5\times10^5$) are orthotopically implanted in the mammary fat pad of BALB/c mice, age 8-weeks, (Harlan, Israel). Tumor size is assessed regularly with Vernier calipers using the formula $width^2 \times length \times 0.5$. When tumors reach a size of 100 $mm^3$, mice are randomly assigned to the following treatment groups (n=6 mice per group): i) control; ii) anti-PD-1 monotherapy; iii) anti-PD-L1 monotherapy; iv) MMP2/MMP9 selective inhibitor SB-3CT monotherapy; v) anti-PD-1 and SB-3CT combination therapy; and vi) anti-PD-L1 and SB-3CT combination therapy. Anti-PD-1, anti-PD-L1 and IgG control antibodies are administered by intraperitoneal injections at a dose of 200 µg/20 g mouse every 3 days. SB-3CT is administered by intraperitoneal injections at a dose of 1 mg/20 g mouse every 3 days. Control mice are injected with IgG antibody and vehicle (10% DMSO in normal saline). Mice receiving either anti-PD-1 or anti-PD-L1 monotherapies are also injected with vehicle (10% DMSO in normal saline). Mice receiving SB3-CT monotherapy are also injected with IgG control antibodies. Tumor growth and mouse survival are monitored. At endpoint (when tumors reach a size of ~1500 $mm^3$ or until experiment reached 27 days), mice are sacrificed.

Figure 1B:
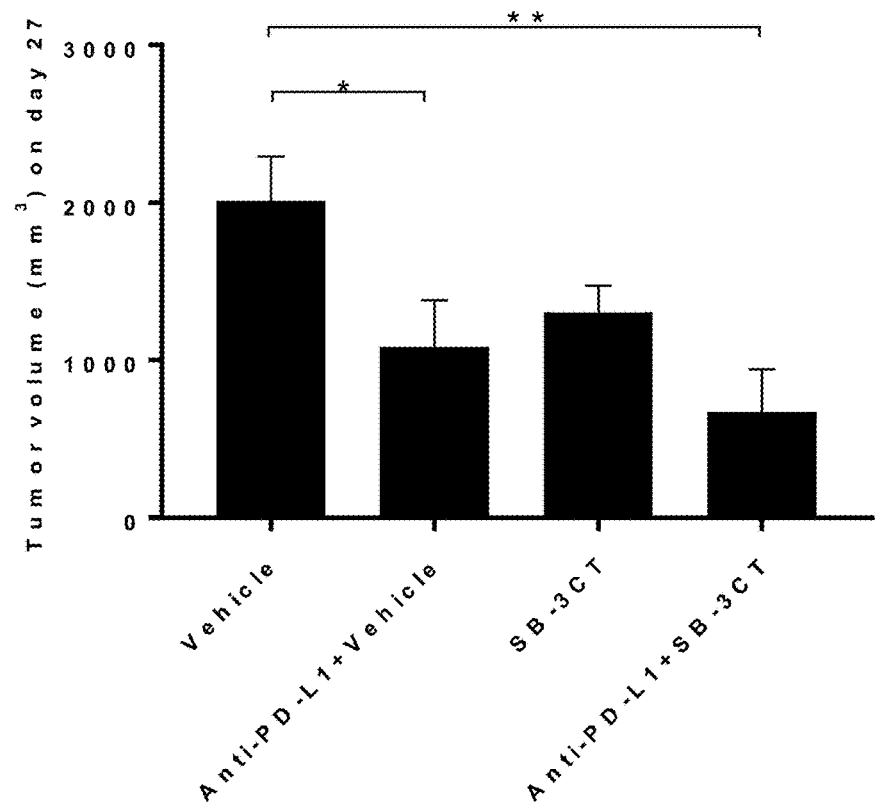
Figure 1C:
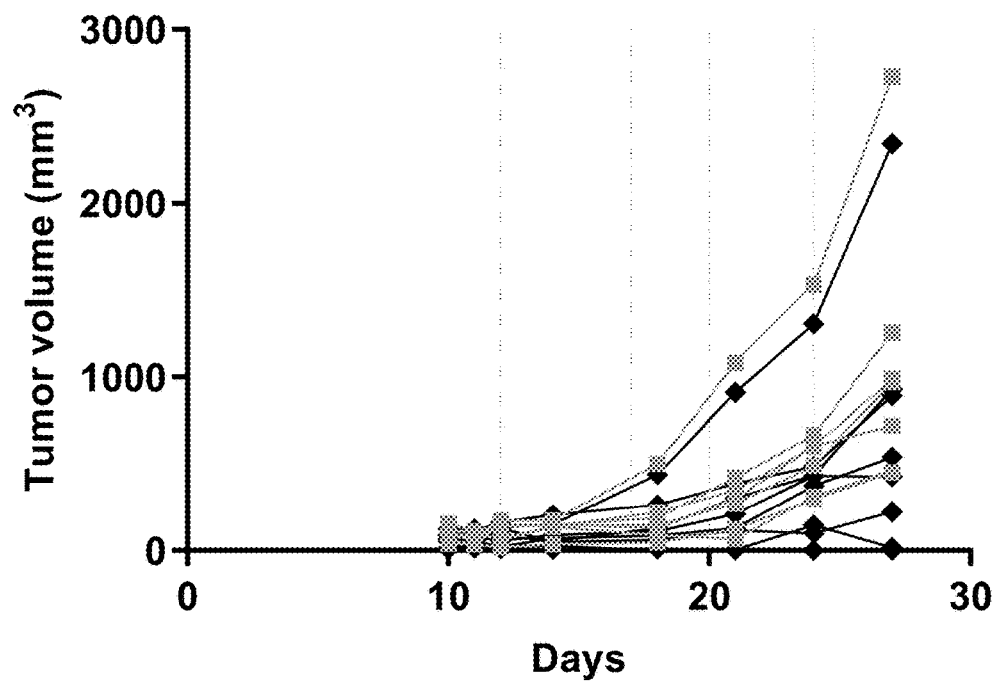
Figure 1D:
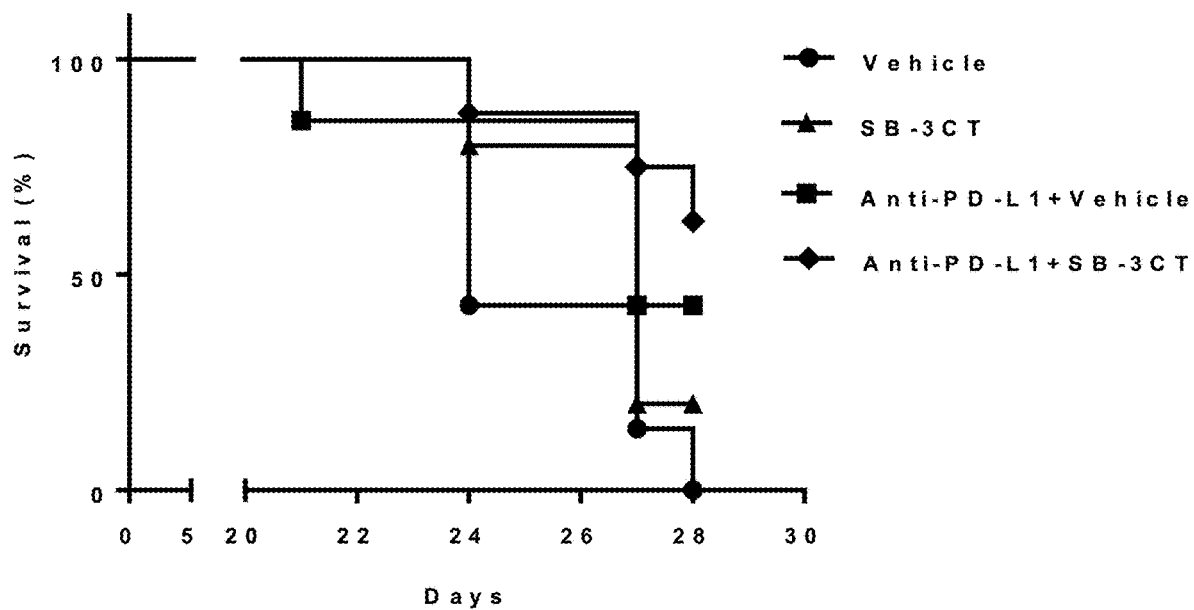

The results, presented in FIGS. 1A and 1B (tumor volume over time and at day 27, the final experimental day, respectively), demonstrate that mice treated with a combination of anti-PD-L1 and the MMP-2/MMP-9 inhibitor SB-3CT, exhibited reduced tumor size compared to mice treated with vehicle, anti-PD-L1 or SB-3CT alone. The advantage of the combined treatment over treatment with the anti-PD-L1 alone was demonstrated by better response rate in individual mice (FIG. 1C, black versus grey, respectively), where it is clearly shown that 3 out of the 8 mice treated with the combined treatment demonstrated reduced tumor size at end point (day 27) compared to the other mice. Moreover, not only the combined treatment inhibited tumor growth, but also improved mice survival (FIG. 1D). Namely, mice treated with the combination therapy exhibited increased survival compared to the control mice, mice treated with anti-PD-L1 or mice treated with SB-3CT. These results suggest that inhibition of MMP-2/MMP-9 together with anti-PD-L1 treatment may improve treatment efficacy.

Example 3. The Effect of Reducing Host-Derived Amphiregulin Levels on ICI Therapy in a Primary Breast Tumor Model Amphiregulin is one of the ligands of the epidermal growth factor receptor (EGFR). Studies have demonstrated a functional role of amphiregulin in several aspects of tumorigenesis. Amphiregulin was chosen in light of our findings described in Example 1 above, which demonstrate that the plasma levels of amphiregulin are increased 2-3 fold in response to anti-PD-L1 treatment in naïve BALB/c and C57/bl/6 mice (Table 4), and 3.7 fold in response to anti-PD-1 treatment in BALB/c mice (Table 5).

Amphiregulin is known to be involved in number of biological processes crucial for tumor development such as proliferation, invasion, angiogenesis, metastasis and resistance to apoptosis, proposing that its expression is indicative of non-responsiveness to cancer treatment. Moreover, Amphiregulin is one of the ligands of an important cancer promoting receptor, Epidermal Growth Factor Receptor (EGFR). As such, it is considered a dominant factor with pro-tumorigenic activities, and its inhibition may improve treatment efficacy.

To investigate whether inhibiting host-derived amphiregulin (which is upregulated in BALB/c mice in response to either anti-PD-1 or anti-PD-L1 treatment) improves the efficacy of anti-PD-L1 therapy, CT26 colon carcinoma cells were subcutaneously implanted into BALB/c mice. When tumors reached a size of 50 mm$^3$, mice were either treated with anti-PD-L1, anti-AREG or anti-PD-L1 and anti-AREG combination therapy while control mice were left untreated. Tumor growth and mouse survival were monitored.

Figure 2A:
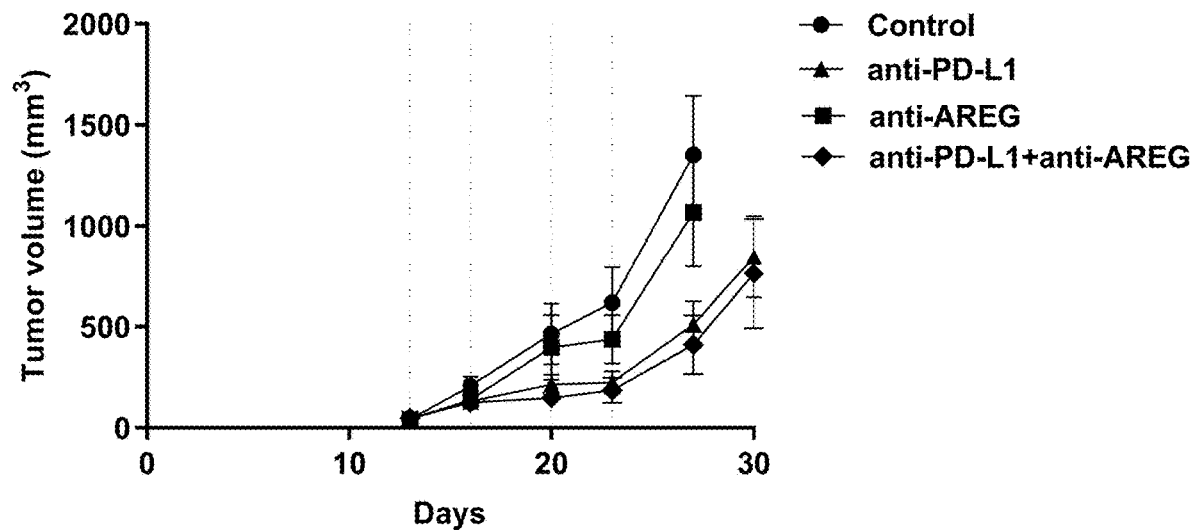
FIGS. 2A-2C show the effect of blocking host-derived amphiregulin on primary tumor growth and survival in a mouse model of colon cancer.
Figure 2B:
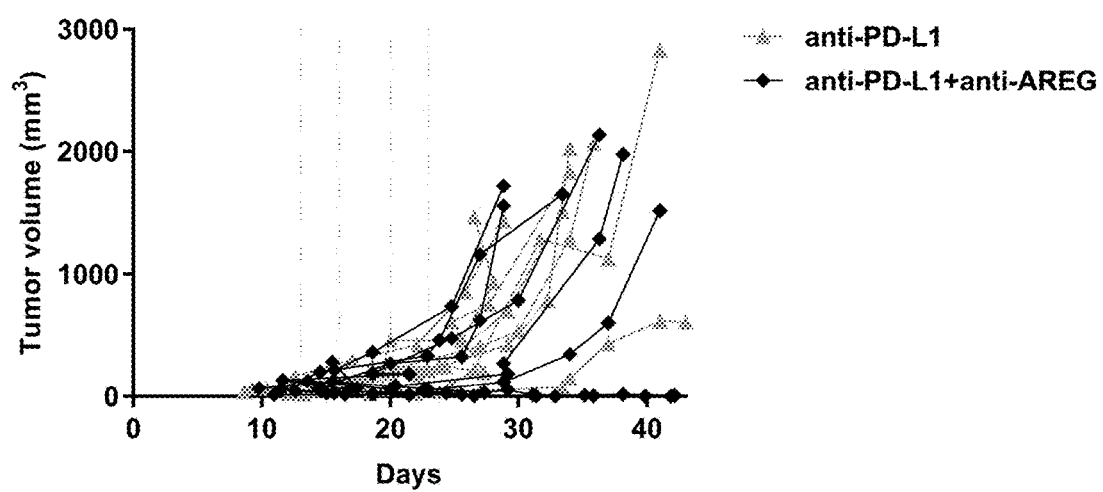
Figure 2C:
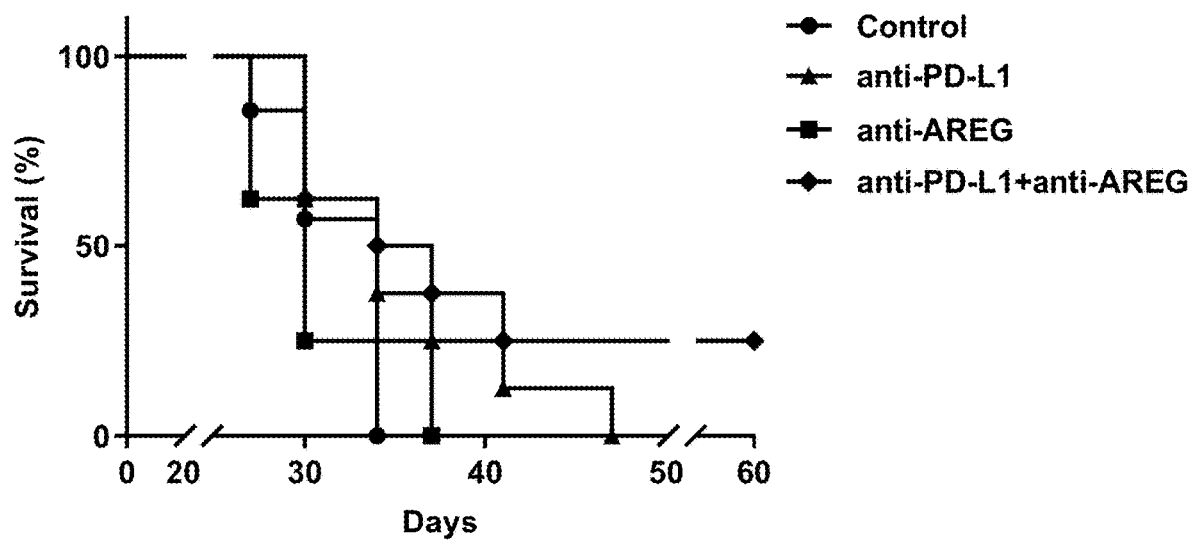
Figure 3:
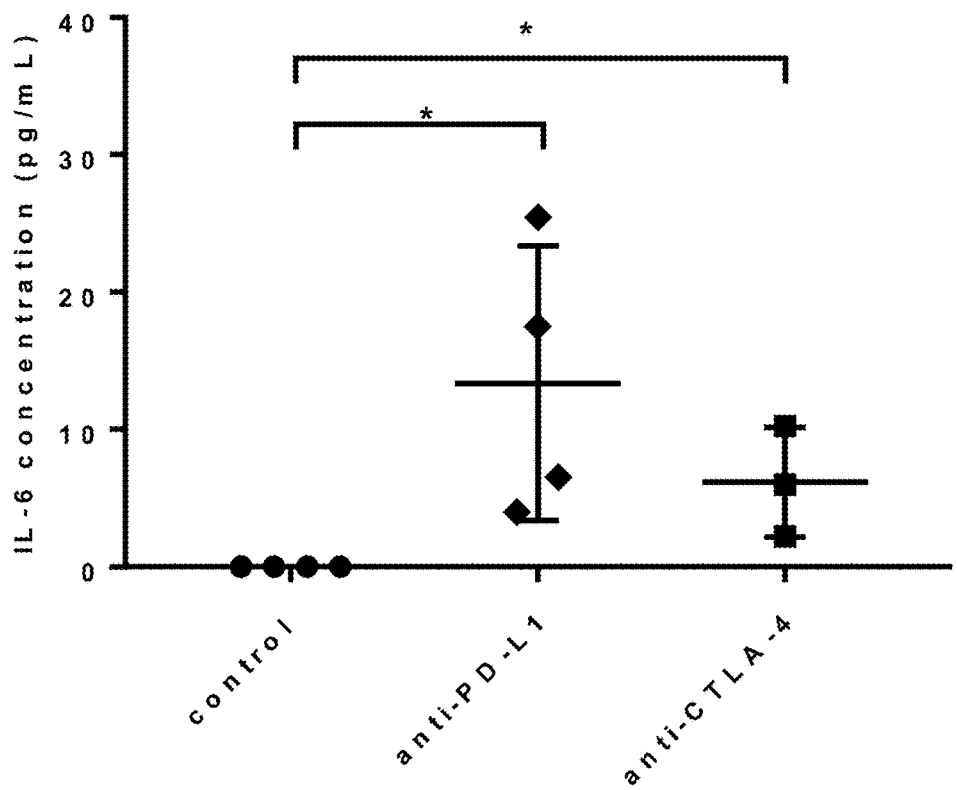
FIG. 3 shows IL-6 expression following treatment with anti-PD-L1 or anti-CTLA-4.

As demonstrated in FIG. 2A, treatment with anti-AREG in combination with anti-PD-L1, exhibited lower tumor growth compared to control mice and anti-AREG-treated mice. While no major difference between the average tumor volume of mice treated with the combined therapy and the anti-PD-L1 was observed, the combined therapy demonstrated a complete response (disappearance of the tumors) in 25% of the treated mice while none of the mice treated with anti-PD-L1 demonstrated this phenomenon (FIG. 2B; The dashed vertical lines represent the days of treatment administration). The higher efficacy of the combined treatment is directly correlated with mice survival (FIG. 2C). Accordingly, mice treated with the amphiregulin inhibitor in combination with anti-PD-L1 have indicated better survival rates compared to control mice, mice treated with anti-PD-L1 or mice treated with anti-AREG monotherapy.

Example 4. IL-6 Expression is Induced in Response to ICI Treatment

IL-6 is another dominant factor that was demonstrated above to be highly induced in response to ICI therapy. As presented, IL-6 was increased by 15.6-fold in response to anti-PD-1 treatment in BALB/c mice (Table 2), 1.7-1.8-fold in response to anti-PD-L1 treatment in nave BALB/c and C57/bl/6 mice (Table 4) and 1.8-fold in response to anti-PD-1 treatment in SCID mice (Table 5).

Figure 4A:
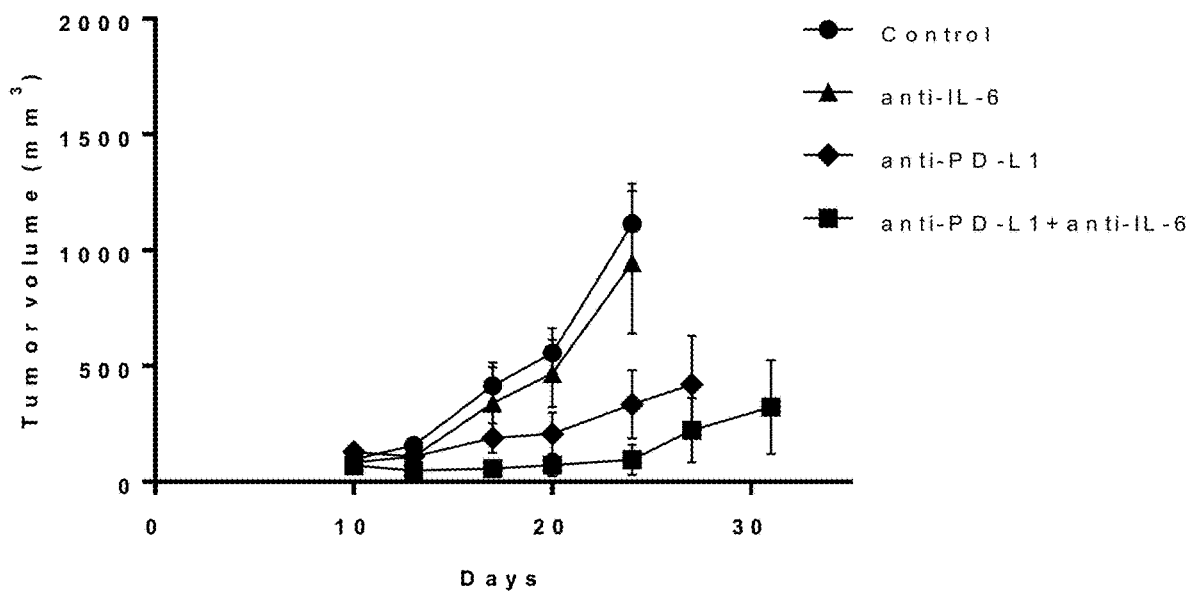
FIGS. 4A-4C show the effect of blocking host-derived IL-6 induced following treatment with anti-PD-L1 on primary tumor growth and mice survival.
Figure 4B:
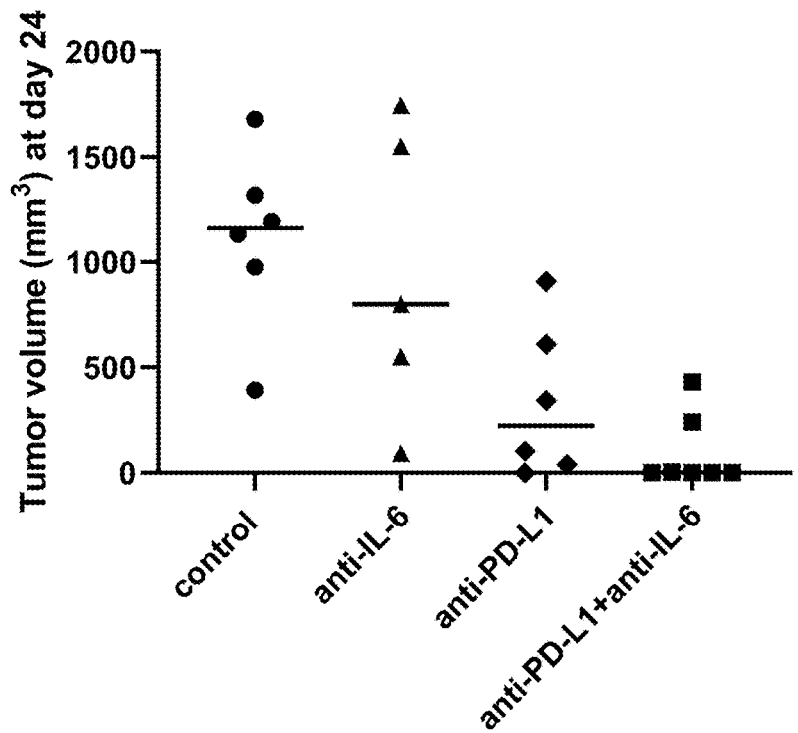
Figure 4C:
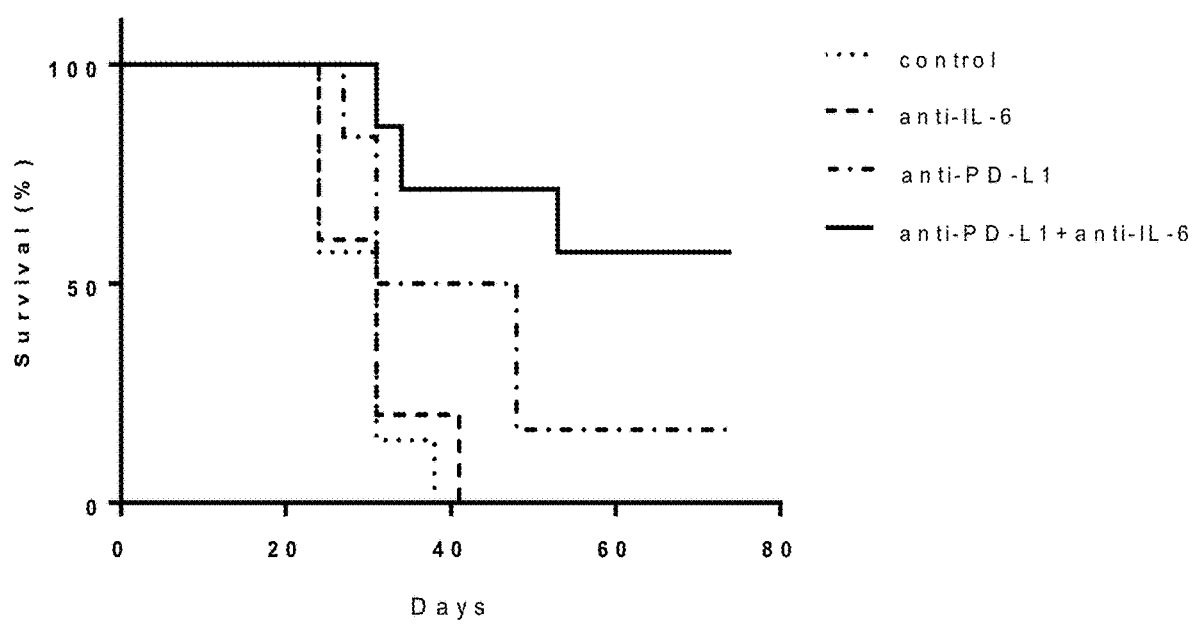

The induction of IL-6 expression following ICI treatment was further validated using ELISA. Mice injected with anti-PD-L1, anti-CTLA-4 or untreated (control mice) were analyzed for IL-6 level in the plasma using ELISA (IL-6 mouse ELISA Kit, ab 100712, Abcam). As shown in FIG. 4, mice treated with anti-PD-L1 and anti-CTLA-4 exhibited a pronounced induction of IL-6 concentration (13.4 and 6.15 pg/ml, respectively) compared to control mice in which IL-6 was undetectable (p values 0.03 and 0.02, respectively). Since this experiment was performed using nave mice, it demonstrates that IL-6 is produced by host cells in response to immune checkpoint inhibitors therapy, independently of tumor presence.

Example 5. Blocking of Anti-PD-L1-Induced Host-Derived IL-6 Inhibits Primary Tumor Growth and Improves Mice Survival IL-6 is known to be involved in number of biological processes crucial for tumor development including proliferation, angiogenesis, inflammation, differentiation and resistance to apoptosis. In addition, IL-6 is a pro-inflammatory cytokine that have been described as a prognostic factor in cancer. Since IL-6 is located at the top of the pro-inflammatory cascade and have been demonstrated to correlate with metastasis it is considered as a dominant factor with pro-tumorigenic and pro-metastatic activities.

For this reason, we tested whether blocking of host-derived IL-6 improves the efficacy of anti-PD-L1 treatment. BALB/c mice were subcutaneously injected with CT26 murine colon carcinoma cells. When tumors reached a size of 50 mm$^3$, mice were IP injected with anti-PD-L1, anti-IL-6, or a combination of the two antibodies and control mice were left untreated. Tumors growth was monitored regularly and when reached a size of 2000 mm$^3$ mice were sacrificed. As demonstrated in FIG. 5A, mice treated with the combination of anti-PD-L1 and anti-IL-6 exhibited reduced tumor growth compared to control, anti-PD-L1 or anti-IL-6 treated mice (p values of 0.003, 0.192 and 0.009, respectively). The advantage of the combined treatment compared to anti-PD-L1 or anti-IL-6 treatments in inhibiting tumor growth was more emphasized when comparing tumor growth in single mice. As demonstrated in FIG. 5B, four out of six mice (57%) treated with anti-PD-L1 in combination with anti-IL-6 showed complete response to the treatment and their tumors disappeared, while in the anti-PD-L1 treated group only one mouse out of the six (16.7%) showed complete response and disappearance of the tumor.

As demonstrated in FIG. 5C, the combined treatment with anti-PD-L1 and anti-IL-6 not only reduced tumor growth but also improved mice survival (undefined median survival) compared to control, anti-PD-L1 or anti-IL-6 treatments (median survival of 31, 39.5 and 31 days, respectively) (p values 0.0026, 0.3552 and 0.0386, respectively), with about 70% survival after 40 days, compared to 50% for the anti-PD-L1 alone group.

Example 6. Blocking of Anti-CTLA-4-Induced Host-Derived IL-6 Inhibits Primary Tumor Growth and Improves Mice Survival To study whether blocking of host-derived IL-6 upregulated in response to anti-CTLA-4 treatment (demonstrated in FIG. 4) improves the efficacy of the treatment, BALB/c mice were orthotopically injected with EMT6 murine breast carcinoma cells into the mammary fat pad. When tumors reached a size of 100 mm$^3$, mice were IP injected with anti-CTLA-4, anti-IL-6 or a combination of anti-CTLA-4 and anti-IL-6 once every three days (a total of 4 injections). Control mice were left untreated. Tumor growth was monitored regularly and when a size of 1500 mm$^3$ was reached, mice were sacrificed.

Figure 5A:
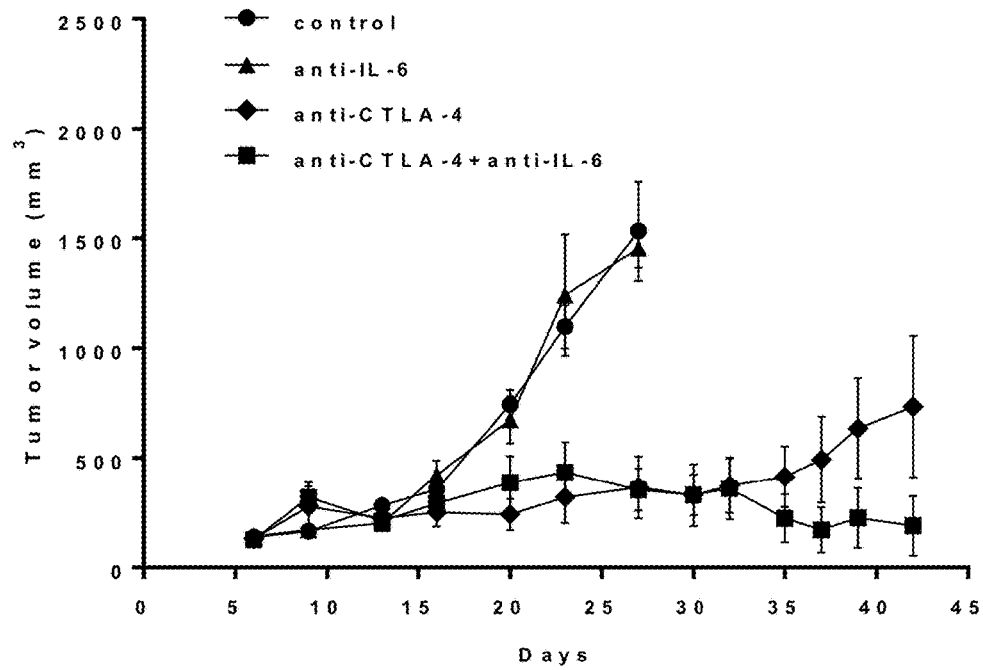
FIGS. 5A-5B show the effect of blocking host-derived IL-6 induced following treatment with anti-CTLA-4 on primary tumor growth and survival. Treatment of BALB/c mice with anti-CTLA-4 resulted in reduced tumor growth (FIG. 5A) and better survival relative to control mice (FIG. 5B), and these effects were further improved by combined treatment with both anti-CTLA-4 and anti-IL-6 antibodies (FIGS. 5A-5B).

FIG. 5A clearly demonstrates enhanced anti-tumor effect of the combined treatment (anti-CTLA-4 and anti-IL-6) compared to the control, anti-CTLA-4 alone or anti-IL-6 treated mice (p values 0.002, 0.137 and <0.001 respectively). Moreover, three out of five mice (60%) treated with the combined treatment of anti-CTLA-4 and anti-IL-6 showed complete response to the treatment and their tumors completely disappeared at about day 35, in contrast to one mouse in the anti-CTLA-4 group, showing that the combined treatment not only inhibited tumor growth but also eradicated the tumor.

Figure 5B:
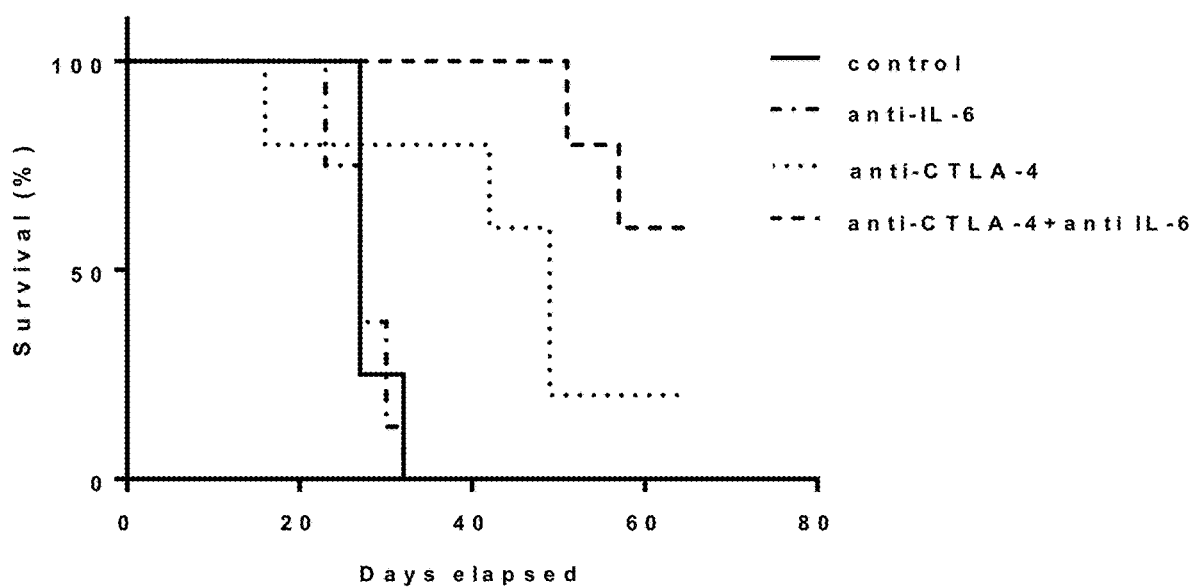

Blocking host-derived IL-6 in combination with anti-CTLA-4 also improved mice survival. As shown in FIG. 5B, mice treated with anti-CTLA-4 in combination with anti-IL-6 exhibited enhanced survival rate (undefined median survival) compared to mice treated with anti-CTLA-4, anti-IL-6 or control mice (median survival of 49, 27 and 27 days, respectively), p values 0.076, 0.0008 and 0.0005, respectively.

The invention claimed is:

1. A method of increasing an anticancer effect of an immune checkpoint inhibitor (ICI) in a cancer patient, the method comprising the steps of:
   (i) calculating a fold change in protein expression for each of a plurality of pro-tumorigenic or pro-metastatic proteins selected from: amphiregulin, IL-6, IL-1Ra, IL-4, PDGFB, TNFA, VEGF, HGF, Endoglin/CD105, GM-CSF, MMP-9, AXL, CD30, HGFR/cMET, ALK-1, Osteoactivin/GPNMB, TNFRII, and VEGFR1 in blood samples obtained from said cancer patient before treatment with said ICI and after treatment with said ICI, wherein said blood samples are selected from the group consisting of blood plasma, whole blood, blood serum and peripheral blood mononuclear cells;
   (ii) for a patient with an increase in protein expression of at least two proteins of said plurality of pro-tumorigenic or pro-metastatic proteins from before treatment to after treatment selecting one of said at least two pro-tumorigenic or pro-metastatic proteins that are increased;
   (iii) selecting a blocking or neutralizing antibody against said selected pro-tumorigenic or pro-metastatic protein, or when said selected protein is any one of amphiregulin, IL-6, IL-1Ra, PDGF-BB, TNFA, and VEGF selecting a blocking or neutralizing antibody against a receptor thereof; and
   (iv) treating said patient with an increase in protein expression with a therapeutically effective amount of the ICI in combination with a therapeutically effective amount of said blocking or neutralizing antibody; thereby increasing an anticancer effect of an ICI in a cancer patient.

2. A method for treatment of a cancer patient non-responsive to treatment with an immune checkpoint inhibitor (ICI) wherein non-responsive comprises at least one of: lack of cancer regression, lack of cancer shrinkage, lack of cancer necrosis, cancer growth, cancer expansion, cancer recurrence and cancer metastases, the method comprising concomitantly administering to the cancer patient a therapeutically effective amount of the ICI and a therapeutically effective amount of a blocking or neutralizing antibody against at least one pro-tumorigenic or pro-metastatic protein selected from Endoglin/CD105, GM-CSF, IL-1rα/IL-1F3, MMP-9, PDGF-BB, TNF-α, VEGF, Axl, CD30, HGF, HGFR/cMET, TNF-RII, ALK-1, Amphiregulin, IL-6, Osteoactivin, and VEGF-R1, wherein the blocking or neutralizing antibody is administered due to the presence of increased protein expression of the at least one pro-tumorigenic or pro-metastatic protein in a blood sample obtained from said cancer patient after treatment with said ICI as compared to a blood sample obtained from said cancer patient before treatment with said ICI, and wherein said blood samples are selected from the group consisting of blood plasma, whole blood, blood serum and peripheral blood mononuclear cells.

3. The method of claim 1, wherein the blood samples before and after treatment are both blood plasma.

4. The method of claim 1, wherein a fold-change of 1.5 or higher is considered an increase in protein expression from before treatment to after treatment.

5. The method of claim 1, wherein the ICI is an inhibitor of an immune checkpoint selected from PD-1, PD-L1, CTLA-4, A2AR, BT-H3, BT-H4, BT-H5; BTLA; IDO1; KIR; LAG-3; TDO; TIM-3; TIGIT; VISTA, and a combination thereof.

6. The method of claim 5, wherein the ICI is selected from: an anti-PD-1 monoclonal antibody selected from Pembrolizumab, Nivolumab, Pidilizumab, Cerniplimab, AMP-224, MEDI0680 and Spartalizumab; an anti-PD-L1 monoclonal antibody selected from Atezolizumab, Avelumab, Durvalumab and MDX-1105; an anti-CTLA-4 monoclonal antibody selected from Ipilimumab and Tremeibnumab, an anti-LAG-3 monoclonal antibody selected from Relatlimab, LAG525 and REGN3767; an anti-TIM-3 monoclonal antibody selected from TSR022 and MBG453; the anti-KIR monoclonal antibody Lirilumab; the anti-TIGIT monoclonal antibody OMP-31M32; the anti-VISTA monoclonal antibody JNJ-61610588 (Onvatilimab); and combinations thereof.

7. The method of claim 1, wherein the patient is treated with:
   (a) a combination of two ICIs, wherein said combination is selected from: Nivolumab (anti-PD-1) and Ipilimumab (anti-CTLA-4); Nivolumab (anti-PD-1) and Atezolimumab (anti-PD-L1); and Durvalumab (anti-PD-L1) and Tremelimumab (anti-CTLA-4);
   (b) a combination of the ICI with an agonistic monoclonal antibody against a T-cell co-stimulatory molecule selected from: CD40, ICOS, OX40, and CD137 (4-IBB); or
   (c) a combination of the ICI with one or more conventional cancer therapies, optionally wherein said conventional therapies are selected from chemotherapy, targeted cancer therapy and radiotherapy.

8. The method of claim 1, wherein the selected pro-tumorigenic or pro-metastatic protein is selected from the group consisting of amphiregulin, and IL-6.

9. The method of claim 8, wherein the selected pro-tumorigenic or pro-metastatic protein is amphiregulin, the ICI is an anti-PD-1 or an anti-PD-L1 monoclonal antibody, and the cancer patient is treated with the ICI in combination with an anti-amphiregulin antibody.

10. The method of claim 8, wherein the selected pro-tumorigenic or pro-metastatic protein is IL-6, the ICI is an anti-CTLA-4, an anti-PD-1 or an anti-PD-L1 monoclonal antibody, and the cancer patient is treated with the ICI in combination with an anti-IL-6 or anti-IL-6 Receptor (anti-IL-6R) agent selected from: (i) an anti-IL-6 monoclonal antibody, or a biosimilar thereof, optionally wherein the anti-IL-6 monoclonal antibody or biosimilar is selected from Siltuximab, Olokizumab, Elsilimomab, Clazakizumab, Gerilimzumab, EBI-031 and Sirukumab; (ii) an anti-IL-6R monoclonal antibody, or a biosimilar thereof, optionally wherein the anti-IL-6R monoclonal antibody or biosimilar is selected from BCD-089, Tocilizumab, LusiNEX, and Sarilumab; (iii) the nanobody Vobarilizumab; and (iv) an IL-6R antagonist optionally wherein the IL-6R antagonist is Olamkicept.

11. The method of claim 1, wherein the cancer is a primary or a metastatic cancer optionally wherein the cancer is selected from bladder, bone, breast, brain, cervical, colon, colorectal, esophageal, gastric cancer, gastrointestinal, glioblastoma, head and neck, head and neck squamous cell cancer, hepatocellular cancer, kidney, liver, lung including small cell lung cancer and non-small cell lung cancer (NSCLC), melanoma, nasopharyngeal, ovarian, pancreas, penile, prostate, skin, testicular, thymus, thyroid, urogenital, or uterine cancer, leukemia, lymphoma, multiple myeloma and sarcoma.

12. The method of claim 1, wherein said after treatment with said ICI is a time after treatment sufficient for the appearance in blood of host-driven resistance factors, optionally wherein said sufficient time after treatment is at least 24 hours after treatment and optionally wherein said before treatment is at most 72 hours before treatment.

13. The method of claim 1, wherein said anticancer effect is selected from inducing cancer regression, inducing cancer shrinkage, inducing cancer necrosis, inhibiting cancer growth, inhibiting cancer expansion, inhibiting cancer recurrence and inhibiting cancer metastases.

14. The method of claim 2, wherein said concomitant administration is after said blood samples from said cancer patient are obtained.

15. The method of claim 1, wherein the ICI is anti-PD-1 and said pro-tumorigenic or pro-metastatic proteins are selected from: GM-CSF, PDGF-BB, IL-1Ra, IL-6, HGF, and MMP-9 or the ICI is anti-PD-L1 and said pro-tumorigenic proteins are selected from: IL-1ra, IL-6, Axl, HGF, and MMP-9.

16. The method of claim 1, wherein step (iii) comprises selecting a blocking or neutralizing antibody against said selected protein.

17. The method of claim 1, wherein said ICI is anti-PD-1 and said pro-tumorigenic or pro-metastatic proteins are selected from IL-6, IL-1Ra, IL-4, PDGF-BB, TNFA, VEGF, HGF, Endoglin/CD105, GM-CSF, MMP-9, ALK-1, Osteoactivin/GPNMB, and VEGFRI or said ICI is anti-PD-L1 and said pro-tumorigenic proteins are selected from IL-6, HGF, GM-CSF, AXL, CD30, HGFR/cMET, ALK-1, Osteoactivin/GPNMB, TNFRII and VEGFRI.

18. The method of claim 2, wherein said ICI is anti-PD-1 and said pro-tumorigenic or pro-metastatic proteins are selected from IL-6, IL-1Ra, IL-4, PDGF-BB, TNFA, VEGF, HGF, Endoglin/CD105, GM-CSF, MMP-9, ALK-1, Osteoactivin/GPNMB, and VEGFRI or said ICI is anti-PD-L1 and said pro-tumorigenic proteins are selected from IL-6, HGF, GM-CSF, AXL, CD30, HGFR/cMET, ALK-1, Osteoactivin/GPNMB, TNFRII and VEGFRI.

* * * * *